United States Patent
Park et al.

(10) Patent No.: US 9,493,746 B2
(45) Date of Patent: *Nov. 15, 2016

(54) ENZYME USED IN BIOSYNTHESIS OF 1, 4-BDO AND SCREENING METHOD OF THE SAME

(71) Applicants: Samsung Electronics Co., Ltd., Suwon-si, Gyeonggi-do (KR); AJOU UNIVERSITY INDUSTRY-ACADEMIC COOPERATION FOUNDATION, Suwon-si, Gyeonggi-do (KR)

(72) Inventors: Jinhwan Park, Suwon-si (KR); Pyungcheon Lee, Suwon-si (KR); Jaechan Park, Yongin-si (KR); Youngmin Lee, Suwon-si (KR); Wooyong Lee, Hwaseong-si (KR); Jinwoo Park, Seoul (KR); Kwangmyung Cho, Seongnam-si (KR); Heejin Hwang, Pyeongtaek-si (KR)

(73) Assignees: SAMSUNG ELECTRONICS CO., LTD., Suwon-Si (KR); AJOU UNIVERSITY INDUSTRY-ACADEMIC COOPERATION FOUNDATION, Suwon-Si (KR)

(*) Notice: Subject to any disclaimer, the term of this patent is extended or adjusted under 35 U.S.C. 154(b) by 14 days.

This patent is subject to a terminal disclaimer.

(21) Appl. No.: 14/504,279

(22) Filed: Oct. 1, 2014

(65) Prior Publication Data
US 2015/0111268 A1    Apr. 23, 2015

Related U.S. Application Data

(63) Continuation-in-part of application No. 13/954,696, filed on Jul. 30, 2013, now Pat. No. 9,121,042.

(30) Foreign Application Priority Data

Jul. 30, 2012  (KR) .................. 10-2012-0083513
Oct. 1, 2013   (KR) .................. 10-2013-0117595

(51) Int. Cl.
  *C12N 9/02*   (2006.01)
  *C12P 7/24*   (2006.01)
  *C12P 7/18*   (2006.01)

(52) U.S. Cl.
  CPC .............. *C12N 9/0008* (2013.01); *C12P 7/18* (2013.01); *C12P 7/24* (2013.01); *C12Y 102/01057* (2013.01); *Y02P 20/52* (2015.11)

(58) Field of Classification Search
  CPC ............................ C12P 7/18; C12N 9/0006
  USPC ............................. 435/189, 252.3; 536/23.2
  See application file for complete search history.

(56) References Cited

U.S. PATENT DOCUMENTS

| 7,858,350 B2 | 12/2010 | Burk et al. | |
| 7,947,483 B2 | 5/2011 | Burgard et al. | |
| 8,129,169 B2 | 3/2012 | Van Dien et al. | |
| 9,121,042 B2* | 9/2015 | Park | C12P 7/18 |
| 2015/0024447 A1* | 1/2015 | Kim | C12P 7/18 435/158 |
| 2015/0111268 A1* | 4/2015 | Park | C12P 7/18 435/147 |

OTHER PUBLICATIONS

AccessionQ7X4B7(2003).*
Hwang et al., "Engineering of a butyraldehyde dehydrogenase of *Clostridium saccharoperbutylacetonicum* to fit an engineered 1,4-butanediol pathway in *Escherichia coli*", Biotechnology and Bioengineering, DOI 10.1002/bit.25196, pp. 1-32 (2013).
U.S. Appl. No. 13/954,696, filed Jul. 30, 2013.

* cited by examiner

*Primary Examiner* — Tekchand Saidha
(74) *Attorney, Agent, or Firm* — Leydig, Voit & Mayer, Ltd.

(57) ABSTRACT

Recombinant butyraldehyde dehydrogenases (Blds) with improved production of 1,4-BDO, as well as recombinant microorganisms comprising polynucleotides encoding the recombinant Blds, and methods of producing 1,4-BDO by using the recombinant microorganisms.

20 Claims, 12 Drawing Sheets

FIG. 6

ENZYME USED IN BIOSYNTHESIS OF 1, 4-BDO AND SCREENING METHOD OF THE SAME

CROSS-REFERENCE TO RELATED APPLICATIONS

This application claims the benefit of Korean Patent Application No. 10-2012-0083513, filed on Jul. 30, 2012 and Korean patent application no. 10-2013-0117595, filed on Oct. 1, 2013, in the Korean Intellectual Property Office, and is a continuation-in-part of co-pending U.S. patent application Ser. No. 13/954,696, filed on Jul. 30, 2013, the entire disclosures of which are hereby incorporated by reference.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: One 93,422 Byte ASCII (Text) file named 718229 _ST25-Revised created on Mar. 11, 2016.

BACKGROUND

1. Field

The present disclosure relates to butyraldehyde dehydrogenases, which are improved for efficient production of 1,4-BDO, and transformed strains containing the same, and methods of producing 1,4-BDO with high-efficiency by using the transformed microorganism.

2. Description of the Related Art 1,4-utanediol(1,4-BDO), as a solvent used annually about 130 million tons worldwide, is produced from petroleum-based substances such as acetylene, butane, propylene, and butadiene.

1,4-BDO is used throughout the chemical industry as a polymer, a solvent, or a fine chemical intermediate of a variety of chemicals. Currently, most chemical substances composed of 4 carbon atoms are derived from 1,4-BDO, maleic anhydride, or the like and are synthesized. However, as oil prices are increasing, the cost of production is also increasing, bringing attention to develop a complementary and an alternative process of chemical production. Herein, a biological process using a microorganism is presented as an alternative to the chemical production process.

Unlike the existing chemical methods, Genometica built a biosynthetic pathway of 1,4-BDO in 2011 by using succinyl-CoA synthetase gene (sucCD) from *Clostridium kluyveri*, CoA-dependent succinate semialdehyde dehydrogenase gene (sucD) from *Porphyromonas gingivalis*, NAD dependent 4-hydroxybutyrate dehydrogenase gene (4hbd) from *P. gingivalis*, 4-hydroxybutyryl CoA:acetyl-CoA transferase gene (cat2) from *P. gingivalis*, and alcohol dehydrogenase gene (adhE2) from *Clostridium acetobutylicum* within *Escherichia coli* (*E. coli*).

According to an embodiment, pathways that are already identified in *E. coli* are modified to construct a new biosynthetic pathway. For example, a microorganism is developed for efficient production of 1,4-BDO with a Bld mutant that is appropriate for the new pathway.

SUMMARY

Provided are recombinant butyraldehyde dehydrogenases (Blds) used to produce 1,4-BDO with high-efficiency. In particular, provided is an isolated, non-naturally occurring (e.g., synthetic or recombinant) polypeptide comprising the amino acid sequence of SEQ ID NO: 1 or a variant thereof comprising a substitution of at least one amino acid selected from the group consisting of Asn409, Arg361, Ala467, Met371, Ala176, Leu273, and Lys279 in the amino acid sequence of SEQ ID NO: 1, wherein the polypeptide catalyzes the conversion of 4-hydroxybutyryl-CoA to 4-hydroxybutyraldehyde.

Provided are transformed (recombinant) microorganisms comprising polynucleotides encoding the recombinant Bld to produce 1,4-BDO with high-efficiency.

Provided are transformed microorganisms comprising polynucleotides encoding the recombinant Bld and butanol dehydrogenase (Bdh) for use in producing 1,4-BDO with high-efficiency.

Provided are transformed microorganisms comprising polynucleotides encoding sucCD (or cat1), sucD, 4hbd, cat2, recombinant Bld, and bdh for use in producing 1,4-BDO with high-efficiency.

Additional aspects will be set forth in part in the description which follows and, in part, will be apparent from the description, or may be learned by practice of the presented embodiments.

BRIEF DESCRIPTION OF THE DRAWINGS

These and/or other aspects will become apparent and more readily appreciated from the following description of the embodiments, taken in conjunction with the accompanying drawings of which:

In FIG. 2, (a) shows the result of E. Coli TOP10 in which a foreign gene is not introduced therein; (b) shows the result of E. Coli TOP in which pSTV-cs4c and pUCM are introduced therein; and (c) shows the result of E. Coli TOP10 in which pSTV-cs4c and pUCM-bld are introduced therein.

FIG. 6 shows common sequences by comparing a butyraldehyde dehydrogenase with sequences of proteins that are predicted to have a similar activity with the butyraldehyde dehydrogenase.

DETAILED DESCRIPTION

Figure 1A:
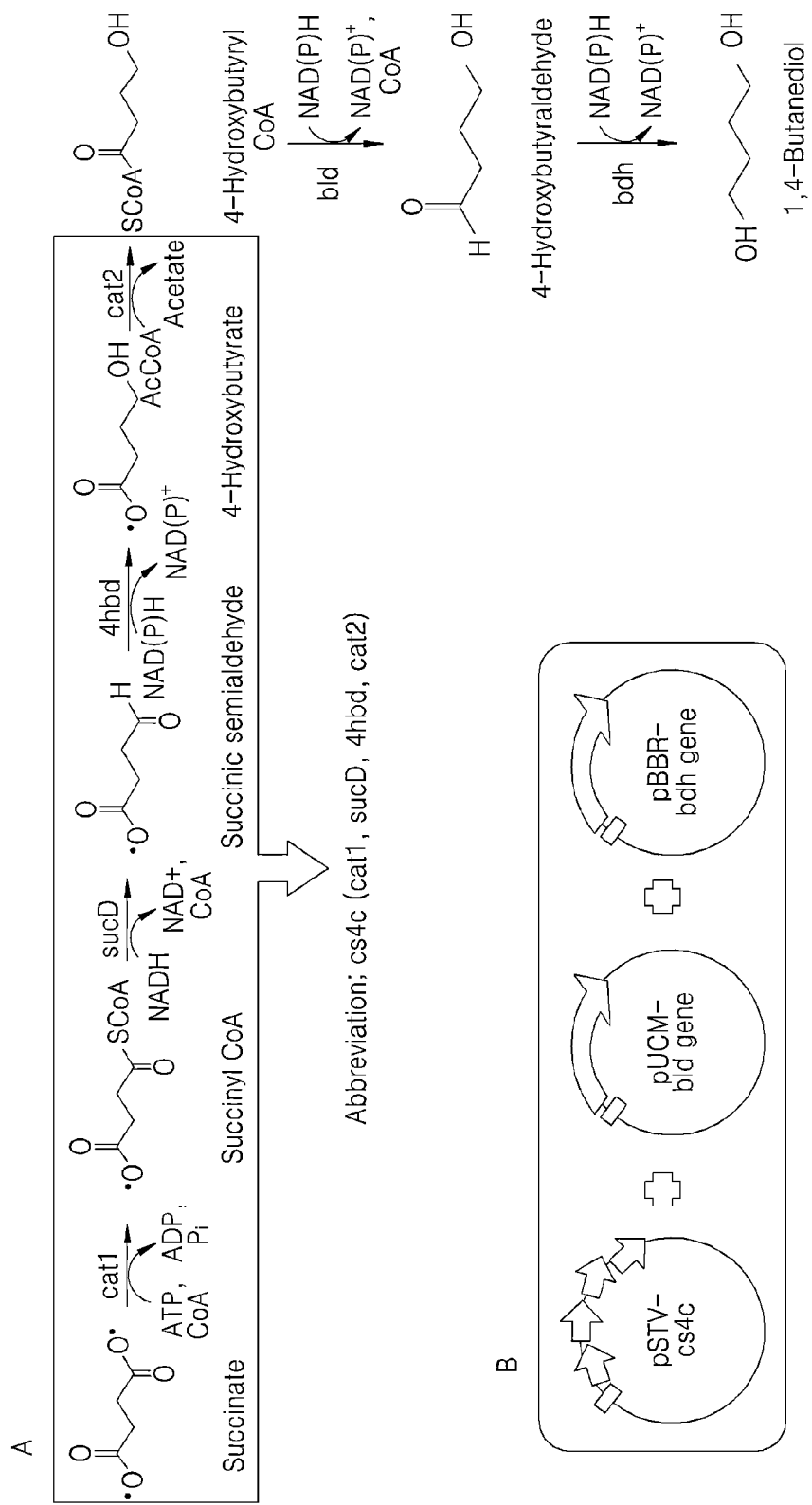
FIG. 1A depicts a biosynthetic pathway of 1,4-BDO built in *E. coli*.
Figure 1B:
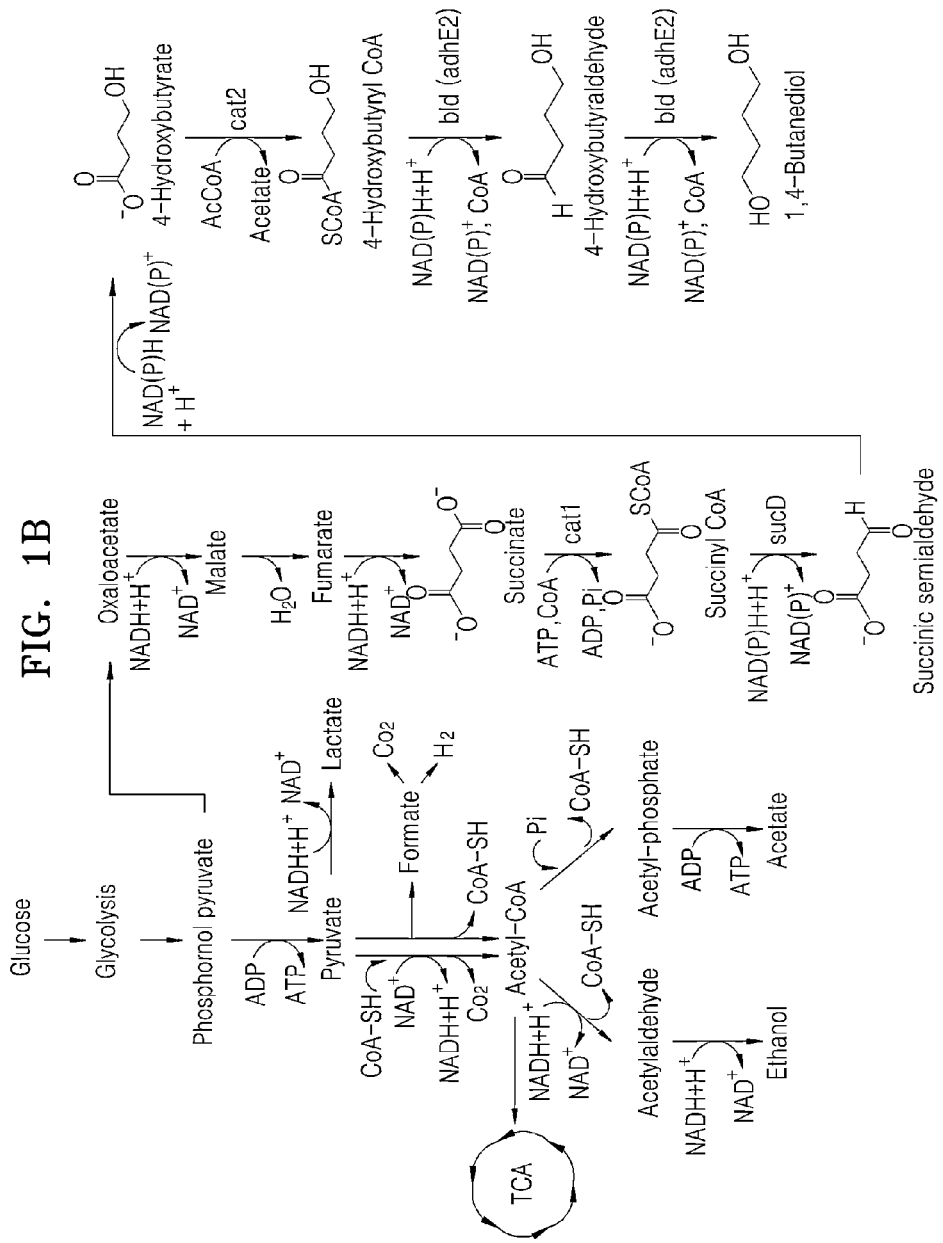
FIG. 1B depicts a biosynthetic pathway of 1,4-BDO built in *E. coli*.
Figure 2:
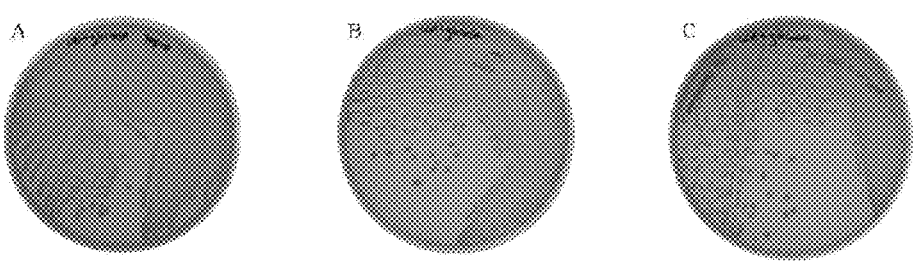
FIG. 2 shows the results of an aldehyde reaction when the supernatant obtained by incubating selected colonies reacts with Schiff's reagent.

One aspect of the present invention provides a recombinant butyraldehyde dehydrogenase (Bld).

According to an aspect of the prevention invention, a butyraldehyde dehydrogenase or a butyraldehyde dehydrogenase mutant having a catalytic activity of converting 4-hydroxybutyryl-CoA into 4-hydroxybutyraldehyde is provided.

The bld may be a gene derived from *Clostridium saccharoperbutylacetonicum*. The Bld may have a polypeptide comprising the amino acid sequence of SEQ ID NO: 1.

The term "polynucleotide" used in the specification comprehensively refers to DNA (gNDA and cDNA) and RNA molecules. A nucleotide, the basic building unit in a polynucleotide, includes not only a natural nucleotide, but also an analogue wherein sugar or a base is modified.

The butyraldehyde dehydrogenase may comprise the amino acid sequence of SEQ ID NO: 1. In addition, the butyraldehyde dehydrogenase mutant may comprise a variant of SEQ ID NO:1, wherein Leu273 is substituted with Ile, Cys, Met, Ser, Thr, or Val. Additionally, the butyraldehyde dehydrogenase mutant may comprise any one of the amino acid sequences selected from the group consisting of SEQ ID NO: 2 to SEQ ID NO: 7

For example, the butyraldehyde dehydrogenase mutant may have a substitution as detailed below:

Asn409 with Thr, Arg361 with Ser, and Ala467 with Ser, in the amino acid sequence of SEQ ID NO: 1;

Arg361 with Ser and Ala467 with Ser in the amino acid sequence of SEQ ID NO: 1;

Met371 with Arg, Arg361 with Ser, and Ala467 with Ser in the amino acid sequence of SEQ ID NO:1;

Ala176 with Thr, Leu273 with Ile, Lys279 with Arg, Arg361 with Ser, and Ala467 with Ser in the amino acid sequence of SEQ ID NO: 1;

Ala176 with Thr in the amino acid sequence of SEQ ID NO: 1;

Leu273 with Ile in the amino acid sequence of SEQ ID NO: 1;

Lys279 with Arg in the amino acid sequence of SEQ ID NO: 1;

Arg361 with Ser in the amino acid sequence of SEQ ID NO: 1;

Ala467 with Ser in the amino acid sequence of SEQ ID NO: 1;

Asn409 with Thr in the amino acid sequence of SEQ ID NO: 1; and/or

Met371 with Arg in the amino acid sequence of SEQ ID NO: 1.

Also, the catalytic site of the mutant may have a substitution of at least one (e.g., 1, 2, 3, 4, 5, 6, 7, 8, 9, 10, 11, 12, 13, 14, 15, or 16) amino acid selected from the group consisting of Thr43, Asn144, Ala241, Gly242, Ala243, Gly244, Pro246, Leu273, Pro274, Ile276, Ala277, Lys279, Glu368, His398, Val432, and Thr441 in the amino acid sequence of SEQ ID NO: 1.

For example, the catalytic site of the mutant may have a substitution of Thr43 with Asp, Asn144 with Asp, Ala241 with Val, Gly242 with Ser, Ala243 with Gly, Gly244 with Ser, Pro246 with Tyr, Leu273 with Ile, Cys, Ser, Thr, or Val, Pro274 with Tyr, Ile276 with Leu, Ala277 with Val, Lys279 with Arg, Glu368 with Gln, His398 with Lys, Val432 with Leu, and Thr441 with Asp in the amino acid sequence of SEQ ID NO: 1.

Also, the mutant may have a substitution of at least one amino acid selected from the group consisting of Met91, Ile139, Thr140, Pro141, Ser142, Thr143, Asn166, Gly167, His168, Pro169, Gly170, Asn201, Pro202, Thr203, Met204, Leu207, Asp208, Ile210, Lle211, Lys212, Thr222, Gly223, Gly224, Pro225, Met227, Thr230, Leu231, Ala241, Gly242, Ala243, Gly244, Leu273, Pro274, Cys275, Ser326, Ile327, Asn328, Lys329, Val332, Thr367, Glu368, Leu369, Met370, and Arg396 in the amino acid sequence of SEQ ID NO: 1 with other amino acid.

For example, the mutant may have a substitution of Met91 with Asp, Ile139 with Leu, Thr140 with Lys, Pro141 with Tyr, Ser142 with Gly, Thr143 with Lys, Asn166 with Asp, Gly167 with Ser, His168 with Lys, Pro169 with Tyr, Gly170 with Ser, Asn201 with Asp, Pro202 with Tyr, Thr203 with Lys, Met204 with Asp, Leu207 with Ile, Asp208 with Asn, Ile210 with Leu, Ile211 with Leu, Lys212 with Thr, Thr222 with Lys, Gly223 with Ser, Gly224 with Ser, Pro225 with His, Met227 with Lys, Thr230 with Lys, Leu231 with Val, Ala241 with Val, Gly242 with Ser, Ala243 with Val, Gly244 with Ser, Leu273 with Ile, Cys, Met, Thr or Val, Pro274 with His, Cys275 with Met, Ser326 with Gly, Ile327 with Leu, Asn328 with Asp, Lys329 with Thr, Val332 with Leu, Thr367 with Lys, Glu368 with Gln, Leu369 with Ile, Met370 with Lys, and Arg396 with Lys in the amino acid sequence of SEQ ID NO: 1.

Thus, provided is an isolated polypeptide comprising the amino acid sequence of SEQ ID NO: 1 with a substitution of at least one amino acid selected from the group consisting of Asn409, Arg361, Ala467, Met371, Ala176, Leu273, and Lys279 in the amino acid sequence of SEQ ID NO: 1 and, optionally, (a) a substitution of at least one amino acid selected from the group consisting of Thr43, Asn144, Ala241, Gly242, Ala243, Gly244, Pro246, Leu273, Pro274, Ile276, Ala277, Lys279, Glu368, His398, Val432, and Thr441 in the amino acid sequence of SEQ ID NO: 1 and/or (b) a substitution of at least one amino acid selected from a group consisting of Met91, Ile139, Thr140, Pro141, Ser142, Thr143, Asn166, Gly167, His168, Pro169, Gly170, Asn201, Pro202, Thr203, Met204, Leu207, Asp208, Lle210, Lle211, Lys212, Thr222, Gly223, Gly224, Pro225, Met227, Thr230, Leu231, Ala241, Gly242, Ala243, Gly244, Leu273, Pro274, Cys275, Ser326, lle327, Asn328, Lys329, Val332, Thr367, Glu368, Leu369, Met370, and Arg396 in the amino acid sequence of SEQ ID NO: 1.

In one embodiment, the butyraldehyde dehydrogenase mutant may be a polypeptide having a sequence set forth in the amino acid sequence of SEQ ID NO: 2, which is a variant of SEQ ID NO: 1 in which Leu273 has been substituted with lle.

In another embodiment, the butyraldehyde dehydrogenase mutant may be a polypeptide having a sequence set forth in SEQ ID NO: 3, which is a variant of SEQ ID NO: 1 in which Leu273 has been substituted with Cys.

In another embodiment, the butyraldehyde dehydrogenase mutant may be a polypeptide having a sequence set forth in SEQ ID NO: 4, which is a variant of SEQ ID NO: 1 in which Leu273 has been substituted with Met.

In another embodiment, the butyraldehyde dehydrogenase mutant may be a polypeptide having a sequence set forth in SEQ ID NO: 5, which is a variant of SEQ ID NO: 1 in which Leu273 has been substituted with Ser.

In another embodiment, the butyraldehyde dehydrogenase mutant may be a polypeptide having a sequence set forth in SEQ ID NO: 6, which is a variant of SEQ ID NO: 1 in which Leu273 has been substituted with Thr.

In another embodiment, the butyraldehyde dehydrogenase mutant may be a polypeptide having a sequence set forth in SEQ ID NO: 7, which is a variant of SEQ ID NO: 1 in which Leu273 has been substituted with Val.

According to another aspect of the present invention, a polynucleotide that encodes the butyraldehyde dehydrogenase or butyraldehyde dehydrogenase mutant is provided. Herein, the polynucleotide may be derived from *Clostridium saccharoperbutylacetonicum*.

According to another aspect of the present invention, a recombinant microorganism that comprises the above-described polynucleotide and is capable of producing 1,4-BDO is provided.

The recombinant microorganism may further include a polynucleotide encoding butanol dehydrogenase (Bdh) having a catalytic activity of converting 4-hydroxybutyraldehyde into 1,4-butanediol. Herein, the polynucleotide encoding bdh may comprise the nucleotide sequence encoding the amino acid sequence of SEQ ID NO: 8. A polynucleotide encoding the butanol dehydrogenase may comprise the nucleotide sequence of SEQ ID NO: 9.

The recombinant microorganism that is capable of producing 1,4-BDO may include an enzyme that converts succinate into succinyl-CoA, an enzyme that converts succinyl-CoA into succinate semialdehyde, an enzyme that converts succinate semialdehyde into 4-hydroxybutyrate, and/or an enzyme that converts 4-hydroxybutyrate into 4-hydroxybutyryl-CoA.

The recombinant microorganism may include a polynucleotide encoding succinyl-CoA:coenzyme A transferase (e.g., cat1) or succinyl-CoA synthetase gene (e.g., sucCD) that converts succinate into succinyl-CoA, a polynucleotide encoding CoA-dependent succinate semialdehyde dehydrogenase (e.g., SucD) that converts succinyl-CoA into succinate semialdehyde, a polynucleotide encoding 4-hydroxybutyrate dehydrogenase (4Hbd) that converts succinate semialdehyde into 4-hydroxybutyrate, and a polynucleotide encoding 4-hydroxybutyryl CoA:acetyl-CoA transferase (Cat2) that converts 4-hydroxybutyrate into 4-hydroxybutyryl-CoA. In one embodiment, the microorganism may be *E. coli* (see, e.g., Yim et al., *Nat. Chem. Biol.*, 7(7): 445-452 (2011).

The enzyme that converts succinate into succinyl-CoA may be succinyl-CoA:coenzyme A transferase (e.g., cat1) belonging to EC 2.8.3.-. The succinyl-CoA:coenzyme A transferase may be Cat1 having the amino acid sequence of SEQ ID NO:10. The gene encoding succinyl-CoA:coenzyme A transferase Cat1 may have the nucleotide sequence of SEQ ID NO: 11.

The enzyme that converts succinyl-CoA into succinate semialdehyde may be CoA-dependent succinate semialdehyde dehydrogenase, and may be classified as an enzyme belonging to EC 1.2.1., such as EC 1.2.1.76. For example, the enzyme may be succinate semialdehyde dehydrogenase (SucD). In addition, the CoA-dependent succinate semialdehyde dehydrogenase may be a gene derived from *E. coli, Clostridium*, or *Porphyromonas*. For example, a sucD protein may have the amino acid sequence of SEQ ID NO: 12. The polynucleotide encoding the SucD may have the nucleotide sequence of SEQ ID NO: 13.

The enzyme that converts succinate semialdehyde into 4-hydroxybutyrate may be 4-hydroxybutyrate dehydrogenase, and may be classified as an enzyme belonging to EC 1.1.1. For example, the enzyme may be NAD-dependent 4-hydroxybutyrate dehydrogenase (4Hbd). Herein, a 4HB dehydrogenase may be a protein derived from *E. coli, Clostridium*, or *Porphyromonas*. For example, a 4Hbd protein may have the amino acid sequence of SEQ ID NO: 14. The polynucleotide encoding the 4HbD may have the nucleotide sequence of SEQ ID NO: 15.

The enzyme that converts 4-hydroxybutyrate into 4-hydroxybutyryl-CoA may be 4-hydroxybutyryl-CoA:acetyl-CoA transferase, and may be classified as an enzyme belonging to EC 2.8.3. For example, the enzyme may be 4-hydroxybutyryl-CoA:acetyl-CoA transferase (Cat2). Herein, a 4-hydroxybutyryl-CoA transferase may be a protein derived from *E. coli, Clostridium*, or *Porphyromonas*. For example, a Cat2 protein may have the amino acid sequence of SEQ ID NO: 16. The polynucleotide encoding the Cat2 may have the nucleotide sequence of SEQ ID NO: 17.

In one embodiment, the recombinant microorganism capable of producing 1,4-BDO may be a recombinant microorganism capable of expressing the sucD protein, the 4Hbd protein, the Cat2 protein, and the Cat1 protein. The recombinant microorganism may be *E. coli*.

The term "protein expression" as used herein denotes that a protein or an enzyme is present in a recombinant microorganism and has an activity. In addition, the protein or the enzyme may be present in a recombinant microorganism by which a polynucleotide encoding a protein in a recombinant microorganism is transcribed to mRNA, and the mRNA is translated to a protein. Herein, the polynucleotide encoding a protein may be inserted into a chromosome in a recombinant microorganism, or may be present within a plasmid vector.

A recombinant microorganism producing a 1,4-BDO compound may be a recombinant microorganism in which a synthesis pathway of lactate from pyruvate is inactivated or reduced. That is, an activity of L-lactate dehydrogenase (Ldh) may be removed or reduced in the recombinant microorganism. The Ldh may have a catalytic activity for converting pyruvate into lactate, and may be classified as an enzyme belonging to EC 1.1.1.27. In addition, an activity of a gene encoding the Ldh may be inactivated or attenuated in the recombinant microorganism.

The term "inactivation" used herein refers to a gene, which is not expressed at all or a gene, which is expressed/generated, but does not have a functional activity, for example, enzymatic activity. The term "attenuation" used herein refers that gene expression is reduced to a level lower than that of a wild strain, a strain that is not engineered, or a parent strain. Alternatively, the term refers that a gene is expressed, but the enzymatic activity thereof is reduced. In the recombinant microorganism, the activity of the Ldh may be reduced to a level less than 30%, 20%, or 10% than that of the Ldh in a wild type recombinant microorganism. In addition, the activity of the Ldh in the recombinant microorganism may be completely removed in the recombinant microorganism. The inactivation or attenuation of genes may be caused by homologous recombination. That is, the inactivation or attenuation of genes may be caused, by which vectors including a partial sequence of the gene sequence are transformed into cells, and the cells are cultured so that the partial sequence may be subjected to homologous recombination with endogenous cellular genes, thereby selecting the recombinant cells by the using selectable markers. The inactivation or attenuation or genes in the recombinant microorganism may result in removal or reduction of the activity of the enzyme encoded by the genes. The term "reduction" used herein refers to a relative activity of a recombinant microorganism that is engineered, compared to an activity of a recombinant microorganism that is not engineered.

The inactivation or attenuation of the lactate dehydrogenase activity in the recombinant microorganism may be caused by an Ldh-coding gene mutant. Such a mutant may be caused by a substitution, a partial or total deletion, or an addition of a nucleotide. In addition, the reduction of the lactate dehydrogenase activity in the recombinant microorganism may be caused by removal of intrinsic genes of the lactate dehydrogenase. Such removal includes not only physical removal of the genes, but also inhibition of functional expression of the genes. In addition, such removal may be caused by homologous recombination.

The term "transformation" used in the specification refers to introduction of genes into a recombinant microorganism for gene expression therein. As long as the transformed genes are expressed in the recombinant microorganism, the transformed genes may be inserted into a chromosome in the recombinant microorganism, or may be present in any location other than the chromosome. In addition, the transformed genes may include polynucleotides such as DNA and RNA, which may encode polypeptides. The transformed genes may be introduced into the recombinant microorganism in any form, so long as they are introduced and expressed therein. For example, the transformed genes may be introduced into the recombinant microorganism in a form of an expression cassette, which is a polynucleotide structure including all the elements necessary for autonomous gene expression. Such an expression cassette typically includes a promoter that is operably linked to the genes, a transcription termination signal, a ribosome-binding site, and a translation termination signal. The expression cassette may be in a form of a vector to enable self-replication. In addition, the transformed genes may be introduced into a host in a form of the gene itself, or in a form of a polynucleotide structure, so as to be operably connected with sequences required for expression in the recombinant microorganism.

Also, a recombinant vector (e.g., expression vector) comprising a polynucleotide that encodes the recombinant Bld is provided.

The term "vector" refers to a DNA composite including DNA sequences operably connected with appropriate regulatory sequences that are capable of expressing DNA within an appropriate host. The vector may be a plasmid vector, a bacteriophage vector, a cosmid vector, a viral vector, or the like.

The vector (e.g., expression vector) can comprise a replication origin, a promoter, a multiple cloning site (MCS), and/or a selection marker. A replication origin enables a plasmid to replicate separately from a chromosome of a host. A promoter functions in the process of transcription of an inserted foreign gene. A MCS enables a foreign gene to be inserted via various restriction enzyme sites, and a selection marker confirms that a vector is properly inserted in a host cell. A selection marker includes antibiotic resistance genes that are commonly used in the art. Examples of the resistance genes are genes that are resistant to ampicillin, gentamicin, carbenicillin, chloramphenicol, streptomycin, kanamycin, geneticin, neomycin, and tetracycline. For example, in consideration of costs, the resistance genes may be genes that are resistant to ampicillin or gentamicin.

When the vector according to the present invention has a prokaryotic cell as a host, the vector may include a strong promoter, such as lambda PL promoter, trp promoter, lac promoter, T7 promoter, or the like. Meanwhile, when the vector has a eukaryotic cell as a host, the vector may include a promoter derived from the genome of mammalian cells (e.g., metallothionein) or a promoter derived from mammalian viruses (e.g., adenovirus late promoter, Vaccinia virus 7.5K promoter, SV40 promoter, cytomegalovirus promoter, and tk promoter of HSV). Exemplary promoters include the lambda PL promoter, trp promoter, lac promoter, or T7 promoter. Such promoters preferably are operably connected (i.e., linked) with foreign polynucleotide sequences (genes or cDNA) that encode a proteins of interest (e.g., Bld or mutants thereof).

The term "operably connected" refers to a functional connection between nucleic acid expression regulatory sequences (e.g., a promoter, a signal sequence, or an array on a transcription regulatory factor-binding site) and other nucleic acid sequences. Due to the operable connection, the regulatory sequences regulate a transcription and/or a translation of the nucleic acid sequences that encode the proteins of interest (e.g., Bld or mutants thereof).

According to another aspect of the present invention, a method of producing 4-hydroxybutyraldehyde includes contacting 4-hydroxybutyryl-CoA with butyraldehyde dehydrogenase or a butyraldehyde dehydrogenase mutant. The butyraldehyde dehydrogenase or butyraldehyde dehydrogenase mutant may comprise, consist essentially of, or consist of the amino acid sequences of SEQ ID NO: 1, 2, 3, 4, 5, 6, or 7, respectively.

According to another aspect of the present invention, a method of producing an 1,4-butanediol includes contacting a 4-hydroxybutyraldehyde with butanol dehydrogenase, thereby producing 1,4-butanediol. The Bdh may be encoded by the nucleotide sequence of SEQ ID NO: 9.

According to another aspect of the present invention, a method of producing 1,4-BDO includes contacting 4-hydroxybutyryl-CoA with Bld or a Bld mutant; and contacting the resultant reaction product with a bdh, thereby producing 1,4-BDO.

According to another aspect of the present invention, a method of producing 1,4-BDO includes introducing butyraldehyde dehydrogenase or a butyraldehyde dehydrogenase mutant, and a bdh to a microorganism; incubating the microorganism; and separating 1,4-BDO from the incubation product. The step of incubating may be culturing the microorganism in a medium to produce 1,4-BDO into the microorganism or into the extracellular medium. The medium any be a liquid or solid medium containing nutrients and/or minerals. The nutrients may include a carbon source, nitrogen source, etc.

In each of the above-described methods, the butyraldehyde dehydrogenase, butyraldehyde dehydrogenase mutant, and/or bdh may be introduced as a polynucleotide (e.g., cDNA or vector) or polypeptide.

Available carbon sources that the microorganism may be monosaccharide, disaccharide, polysaccharide, or the like. For example, glucose, fructose, mannose, galactose, or the like may be used. Also, available nitrogen sources that the microorganism may be organic nitrogen compounds, inorganic nitrogen compounds, or the like. For example, amino acids, amides, amines, nitrates, ammonium salts, or the like may be used. An oxygen condition for incubating the microorganism may be an aerobic condition of normal oxygen partial pressure, a hypoxic condition containing from larger than 0 to 10%, for example, 0.1~10% oxygen of the saturation concentration, or an oxygen-free anaerobic condition.

The term "microaerobic condition" used herein refers to a condition having less oxygen than oxygen concentration obtained when the culture medium is in contact with a normal atmosphere. The microaerobic condition or anaerobic condition may be formed by, for example, supplying carbon dioxide or nitrogen at a flow rate in a range of about 0.1 to about 0.4 volume per volume per minute (vvm), for example, about 0.2 to about 0.3 vvm, or about 0.25 vvm. In addition, the microaerobic condition or the anaerobic condition may have a flow rate in a range of about 0 to about 0.4 vvm, about 0.1 to about 0.3 vvm, about 0.15 to about 0.25 vvm.

The introduction steps of the above-described methods may include introducing a polynucleotide (e.g., gene or cDNA) encoding sucCD or Cat1 that converts succinate into succinyl CoA, a polynucleotide (e.g., gene or cDNA) encoding sucD that converts succinyl-CoA into succinate semialdehyde, a polynucleotide (e.g., gene or cDNA) encoding 4hbd that converts succinate semialdehyde into 4-hydroxybutyrate, and a polynucleotide (e.g., gene or cDNA) encoding cat2 that converts 4-hydroxybutyrate into 4-hydroxybutyryl-CoA.

According to another aspect of the present invention, a method of confirming the yield of 1,4-BDO comprises introducing Bld or a Bld mutant to a microorganism; contacting the microorganism with Schiff's reagent; and measuring absorbance. Herein, the confirmation of the yield of 1,4-BDO yield is performed by measurement of the yield of 4-hydroxybutyraldehyde.

EXAMPLES

Reference will now be made in detail to embodiments, examples of which are illustrated in the accompanying drawings, wherein like reference numerals refer to the like elements throughout. In this regard, the present embodiments may have different forms and should not be construed as being limited to the descriptions set forth herein. Accordingly, the embodiments are merely described below, by referring to the figures, to explain aspects of the present description.

Example 1

Host Cell for Transformation and Manufactured Expression Vector for Transformation Recombinant microorganisms used to efficiently produce 1,4-BDO and expression vectors used to transform the microorganisms are shown in Table 1 below.

TABLE 1

| Strains and plasmids | Relevant properties | Source or reference |
|---|---|---|
| Strains | | |
| *Escherichia coli* XL1-Blue | F'::Tn10 proA+B+ lacIq Δ(lacZ)M15/recA1 endA1 gyrA96 (Nalr) thihsdR17 (rK−mK+) glnV44 relA1 lac | Stratagene |
| *E. Coli* TOP10 | F- mcrA Δ(mrr-hsdRMS-mcrBC) φ80lacZΔM15 ΔlacX74 nupG recA1 araD139 Δ(ara-leu)7697 galE15 galK16 rpsL(StrR) endA1 | Invitrogen |
| *E. Coli* BL21 (DE3) | F- ompT gal [dcm] [lon] hsdSB (rB− mB−; an *E. coli* B strain) with DE3, a λ prophage carrying the T7 RNA polymerase gene | NEB |
| *Clostridium saccharoperbutylacetonicum* KCTC 5577 | Source for bld and bdh | KCTCa |
| *Clostridium acetobutylicum* KTCT 1790 | Source for adh1, adhE1, adhE2, bdhA, and bdhB | KCTC |
| Plasmids | | |
| pUCM | Cloning vector modified from pUC19; constitutive lac promoter, Apr | (Kim et al., 2010) |
| pUCM-bld | Constitutively expressed bld of *C. saccharoperbutylacetonicum* | This study |
| pUCM-adh1 | Constitutively expressed adh1 of *C. acetobutylicum* | This study |
| pUCM-adhE1 | Constitutively expressed adhE1 of *C. acetobutylicum* | This study |
| pUCM-adhE2 | Constitutively expressed adhE2 of *C. acetobutylicum* | This study |
| pUCM-bdhA | Constitutively expressed bdhA of *C. acetobutylicum* | This study |
| pUCM-bdhB | Constitutively expressed bdhB of *C. acetobutylicum* | This study |
| pUCM-bdh | Constitutively expressed bdh of *C. saccharoperbutylacetonicum* | This study |

TABLE 1-continued

| Strains and plasmids | Relevant properties | Source or reference |
|---|---|---|
| pUCM-bld-M1-5 series | Constitutively expressed bld mutant 1-5 generated by random mutagenesis | This study |
| pUCM-bld-S1-6 series | Constitutively expressed Bld mutant A176T, L273I, K279R, M371R, N409T, or A467S. | This study |
| pUCM-bld-L273X series | Constitutively expressed 18 Bld mutants having different amino acids at the position of Leu273 except for L273I | This study |
| pBBR1MCS2 | Broad-host-range plasmid, Kmr | (Kovach et al., 1995) |
| pBBR-bdh | Constitutively expressed bdh of C. saccharoperbutylacetonicum, Kmr | This study |
| pBBR-bdhA | Constitutively expressed bdhA of C. acetobutylicum | This study |
| pBBR-bdhB | Constitutively expressed bdhB of C. acetobutylicum | This study |
| pSTV28 | Plasmid with a replication origin of pACYC184, Cmr | Takara |
| pSTV-cs4c | Constitutively expressed cat1, sucD, 4hbd, and cat2 together | This study |
| pET21a | f1 origin, T7 promoter, C-terminal His-tag sequence, Apr | Novagen |
| pET-bld_WT | Inducible expression of Hig6-tagged wild-type Bld on pET21a | This study |
| pET-bld_L273I | Inducible expression of Hig6-tagged Bld L273I on pET21a | This study |
| pET-bld_L273T | Inducible expression of Hig6-tagged Bld L273T on pET21a | This study |
| pET-AdhE2 | Inducible expression of Hig6-tagged AdhE2 on pET21a | This study |
| pET-Bdh | Inducible expression of Hig6-tagged Bdh on pET21a | This study |

1. Kim, S. H., Y. H. Park, C. Schmidt-Dannert, and P. C. Lee. 2010. Redesign, reconstruction, and directed extension of the brevibacterium linens C40 carotenoid pathway in *Escherichia coli*. Applied and Environmental Microbiology 76:5199-5206.
2. Kovach M E. Et al., 1995. Four new derivatives of the broad-host-range cloning vector pBBR1 MCS, carrying different antibiotic-resistance cassettes. Gene 166:175-176.

Example 2

Modularization of Biosynthetic Pathway Genes cat1-sucD-4hbd-cat2 genes synthesized in a pGEM vector were cloned at positions of Xba I and Not I of a pUCM vector with a promoter. Then, subcloning was performed at positions of Sac I and BamH I of a pSTV 28 vector to obtain pSTV28-cs4C (SEQ ID NO:98).

AdhE2 was amplified from *Clostridium acetobutylicum*'s chromosomal DNA by PCR, and then, cloning was performed at positions of Xba I and Not I of pUCM vector. PCR was performed by using DNA engine thermal cycler (Bio-Rad), for 4 minutes at the temperature of 95° C., following by 1 minute at the temperature of 94° C., 40 seconds at the temperature of 50° C., and 1 minute at the temperature of 72° C., and the latter three processes were repeatedly performed 32 times. Finally the PCR was further performed at the temperature of 72° C. for 7 minutes.

DNA sequences for each primer are shown in Table 2 below.

TABLE 2

| Gene | Sequence | SEQ ID NO | Enzyme site |
|---|---|---|---|
| bdh | F; 5'-GCTCTAGAAGGAGGATTACAAAATGGAGAATTTTAGATTTAATG | SEQ ID NO: 18 | Xba I |
| | R; 5'-TTCCCTTGCGGCCGCTTAAAGGGACATTTCTAA | SEQ ID NO: 19 | Not I |
| bld | F; 5'-GCCCCGGGAGGAGGATTACAAAATGATTAAAGACACGCTAGTTTC | SEQ ID NO: 20 | Xma I |
| | R; 5'-TTCCCTTGCGGCCGCTTAACCGGCGAGTACACATC | SEQ ID NO: 21 | |
| cs4c | F; 5'-GCTCTAGAAGGAGGATTACAAAATGAGTAAAGGGATTAAGAAC | SEQ ID NO: 22 | Xba I |
| | R; 5'-TTCCCTTGCGGCCGCTTAACCAAAACGTTTGCG | SEQ ID NO: 23 | Not I |
| Sub_BamHI_R | R; 5'-CGGGATCCCGGTGTGAAATACCG | SEQ ID NO: 24 | BamH I |
| Sub_EcoRI_R | R; 5'-GAATTCCGGTGTGAAATACCG | SEQ ID NO: 25 | EcoR I |

TABLE 2-continued

| Gene | Sequence | SEQ ID NO | Enzyme site |
|---|---|---|---|
| Sub_SacI_FF; | 5'-GAGCTCCCGACTGGAAAGCG | SEQ ID NO: 26 | Sac I |
| Sub_SalI_FF; | 5'-ACGCGTCGACCCGACTGGAAAGCG | SEQ ID NO: 27 | SalI |
| adhE2 | F; 5'-GCTCTAGAAGGAGGATTACAAAATGATTTTGCATCTGCTG | SEQ ID NO: 28 | XbaI |
|  | R; 5'-TTCCCTTGCGGCCGCTTAAAACGACTTGATGTAGAT | SEQ ID NO: 29 | NotI |
| adh1 | F; 5'-GCTCTAGAAGGAGGATTACAAAATGATGAGATTTACATTACCAAG | SEQ ID NO: 30 | XbaI |
|  | R; 5'-TTCCCTTGCGGCCGCTTAAAAATCAACTTCTGTACC | SEQ ID NO: 31 | NotI |
| adhE1 | F; 5'-GCTCTAGAAGGAGGATTACAAAATGAAAGTCACAACAGTAAAG | SEQ ID NO: 32 | XbaI |
|  | R; 5'-TTCCCTTGCGGCCGCTTAAGGTTGTTTTTTAAAAC | SEQ ID NO: 33 | NotI |
| adhE2 | F; 5'-GCTCTAGAAGGAGGATTACAAAATGATTTTGCATCTGCTG | SEQ ID NO: 34 | XbaI |
|  | R; 5'-TTCCCTTGCGGCCGCTTAAAACGACTTGATGTAGAT | SEQ ID NO: 35 | NotI |
| bdhA | F; 5'-GCTCTAGAAGGAGGATTACAAAATGCTAAGTTTTGATTATTCA | SEQ ID NO: 36 | XbaI |
|  | R; 5'-TTCCCTTGCGGCCGCTTATAAGATTTTTTAAATATCTC | SEQ ID NO: 37 | NotI |
| bdhB | F; 5'-GCCCCGGGAGGAGGATTACAAAATGGTTGATTTCGAATATTCAATAC | SEQ ID NO: 38 | XmaI |
|  | R; 5'-TTCCCTTGCGGCCGCTTACACAGATTTTTTGAATATTTG | SEQ ID NO: 39 | NotI |
| bld (pET21a) | F; 5'-GCGAATTCATGATTAAAGACACGCTAGTTTC | SEQ ID NO: 40 | EcoRI |
|  | R; 5'-AAAACTCGAGACCGGCGAGTACACATCT | SEQ ID NO: 41 | XhoI |
| adhE2 (pET21a) | F; 5'-GCGGATCCATGATTTTGCATCTGCTGCGA | SEQ ID NO: 42 | BamHI |
|  | R; 5'-AAAACTCGAGAAACGACTTGATGTAGATATCC | SEQ ID NO: 43 | XhoI |
| bdh (pET21a) | F; 5'-GCGAATTCATGGAGAATTTTAGATTTAAT | SEQ ID NO: 44 | EcoRI |
|  | R; 5'-AAAACTCGAGAAGGGACATTTCTAAAATTTTATA | SEQ ID NO: 45 | XhoI |

Example 3

Genetic Screening of Bld and Bdh Genes

In order to produce 4-hydroxybutyryl-CoA in *E. coli*, a vector (pSTV-cs4C) was manufactured. The synthesized CS4C was used to express cat1 genes, sucD genes, 4hbd genes, and cat2 genes. In the case of expression of the CS4C module, 1,4-BDO is manufactured in a small amount (about up to 2.0 mg/L). In order to examine the production of 1,4-BDO, Bld, Adh1, and AdhE2 were analyzed. As a result, it was found that the Bld was an enzyme converting 4-hydroxybutyryl-CoA into 4-hydroxybutyraldehyde. Regarding the production of 1,4-BDO with respect to the three candidates above, i.e., Bld, Adh1, and AdhE2, it was confirmed that 29 mg/L of 1,4-BDO was produced with respect to AdhE2, 10 mg/L of 1,4-BDO was produced with respect to bld, and 1.8 mg/L of 1,4-BDO was produced with respect to Adh1.

Thereafter, the production of 1,4-BDO was confirmed with respect to the CS4C module, bld, and three candidates, i.e., Bdh, BdhA, and BdhB. It was confirmed that Bdh has a catalytic activity for converting 4-hydroxybutyraldehyde into 1,4-BDO. As a result of the expression, with respect to the CS4C module, bld, and each of 3 enzymes, 1,4-BDO was produced as the following. 19 mg/L of 1,4-BDO was produced with respect to Bdh, 16 mg/L of 1,4-BDO was produced with respect to BdhB, and 15 mg/L of 1,4-BDO was produced with respect to BdhA.

Example 4

Genetic Improvement and Screening

<4-1> Manufacture of Bld Mutants

A bld gene was transformed by directed evolution to increase the production of 1,4-BDO. Sequences of the bld gene were changed by error prone PCR. In this regard, 2.5 mM MgCl$_2$ and a subcloning primer were used. By using G-rich dNTP (T:A:C:G=1:1:1:4) and T-rich dNTP (T:A:C:G=4:1:1:1) separately, a variety of errors were increased. These bld mutants were inserted at positions of Xma I and Not I of a pUCM vector to produce pUCM-bld.

<4-2> Screening of Bld mutants for highly efficient production of 1,4-BDO pUCM-bld was introduced to TOP10 to which the pSTV 28-sucCD-sucD-4hbd-cat2 (pSTV-cs4c) vector was introduced.

Figure 3:
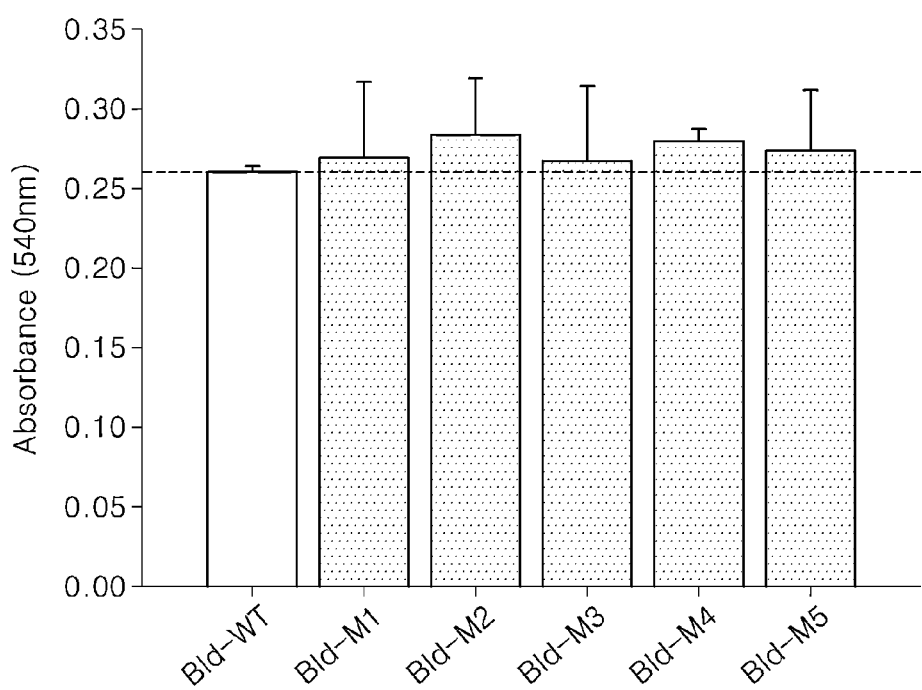
FIG. 3 is an absorbance graph obtained at a wavelength of 540 nm after 1 hour of the reaction showing the results of an aldehyde reaction when the supernatant obtained by incubating selected colonies reacts with Schiff's reagent. A bld with a good activity results in the production of a lot of 4-hydroxybutyraldehydes, which is confirmed to be useful in a screening method using Schiff's reagent.

Schiff's reagent was used to search for a bld mutant that is capable of increasing the yield among libraries. Schiff's reagent was a solution including 30 mg/ml sodium bisulfate (in water), 0.5 M KCl (in water), and 2 mg/ml pararosaniline (in ethanol) which were mixed at a ratio of 2:1:2, and the solution was added to 0.8% agar (in water) for reaction on a plate with colonies floating thereon. After mixing the two solutions, the mixture was poured onto a plate and a reaction was performed at 37° C. for 3 hours. Then, red colonies were selected and incubated on 2 ml LB culture under the conditions of 37° C., 250 rpm, and 12 hours. 200 µl of the supernatant (obtained by centrifuging 1 ml of the culture medium at 13,000 rpm for 10 minutes) and 100 µl of Schiff's reagent were mixed together and reacted at 37° C. for about 1 to 5 hours. Absorbance was measured at 540 nm. Colonies showing high absorbance were introduced to E. Coli TOP 10 along with pSTV-cs4c and pBBR-bdh and incubated (see FIG. 3).

Example 5

E. coli Incubation and 1,4-BDO Production

E. coli strain TOP10 was used to produce 1,4-BDO by the cloning and expression of the gene modules.

Recombinant E. coli including 3 plasmids (pSTV-cs4c, pBBR-bdh, and pUCM-bld) were incubated using a serum bottle under anaerobic conditions of 30° C., 250 rpm, and 48 hours. The medium composition was 100 ml of LB containing 0.6% calcium carbonate and 2% glucose, and 50 µg/ml chloramphenicol, 100 µg/ml ampicillin, and 50 µg/ml kanamycin were all added thereto.

An incubation condition was prepared as an anaerobic condition by injecting nitrogen and the incubation was performed at 30° C., 250 rpm, and 18 hours. The medium composition was 1 L of LB medium including 2% glucose, and 50 µg/ml chloramphenicol, 100 µg/ml ampicillin, and 50 µg/ml kanamycin were all added thereto.

When the modulated genes that were associated with biosynthesis of 1,4-BDO were transformed within E. coli by the method mentioned above, the recombinant E. coli produced 1,4-BDO. However, less 1,4-BDO was produced since 4-hydroxybutyrate accumulated first. Therefore, experiments were designed in a way that 4-hydroxybutyraldehydes were produced in great quantities to make a biosynthetic pathway towards 1,4-BDO.

Example 6

Analysis of 1,4-BDO 1 ml of 100 ml culture obtained in Example 4 was extracted and centrifuged at 13000 rpm for 30 minutes, and the supernatant was centrifuged again under the same condition. Then 800 µl was filtered through a 0.45 um filter to prepare a sample. 10 µl of the sample was used for HPLC analysis. HPLC was performed by using Agilent 1100 device equipped with Refractive index detector (RID). 4 mM $H_2SO_4$ solution was used as a mobile phase and BIO-RAD Aminex HPX-87H Column was used as a stationary phase wherein the flow rate is 0.7 ml/min. Temperature of the column and detector was both 50° C.

The yield of 1,4-BDO was analyzed and results show that more 1,4-BDO was produced when the mutant bld gene was introduced and incubated than when the existing Bld gene was expressed with cs4c and bdh genes within E. coli TOP10. The Bld-M2 sample produced about 0.04 g/L concentration of 1,4-BDO, more than twice compared to others (see FIG. 4). Bld-M1, Bld-M3, Bld-M4, and Bld-M5 samples also showed higher 1,4-BDO productivity than the control (Bld-WT) (see FIG. 4). As a result of analyzing nucleotide sequences of the Bld mutants, the sequences were identified as shown in Table 3.

From the results above, it was confirmed that when the butyraldehyde dehydrogenase has high activity, more 4-hydroxybutyraldehyde was produced, and the hydroxybutyraldehyde bound to Schiff's reagent to produce color, which is useful for screening.

TABLE 3

| Mutant | Nucleotide Mutation | Amino Acid Mutation |
|---|---|---|
| Bld-M1 | AAC → ACC | N409T |
|  | AGG → AGT | R361S |
|  | GCC → TCC | A467S |
| Bld-M2 | AGG → AGT | R361S |
| Bld-M3 | AGG → AGT | R361S |
|  | GCC → TCC | A467S |
| Bld-M4 | AGG → AGT | R361S |
|  | ATG → AGG | M371R |
|  | GCC → TCC | A467S |
| Bld-M5 | GCT → ACT | A176T |
|  | TTA → ATA | L273I |
|  | AAA → AGA | K279R |
|  | AGG → AGT | R361S |
|  | GCC → TCC | A467S |
| Bld-S1 | GCT → ACT | A176T |
| Bld-S2 | TTA → ATA | L273I |
| Bld-S3 | AAA → AGA | K279R |
| Bld-S4 | ATG → AGG | M371R |
| Bld-S5 | AAC → ACC | N409T |
| Bld-S6 | GCC → TCC | A467S |

Example 7

Screening the Most Effective Bld Mutant

Figure 4:
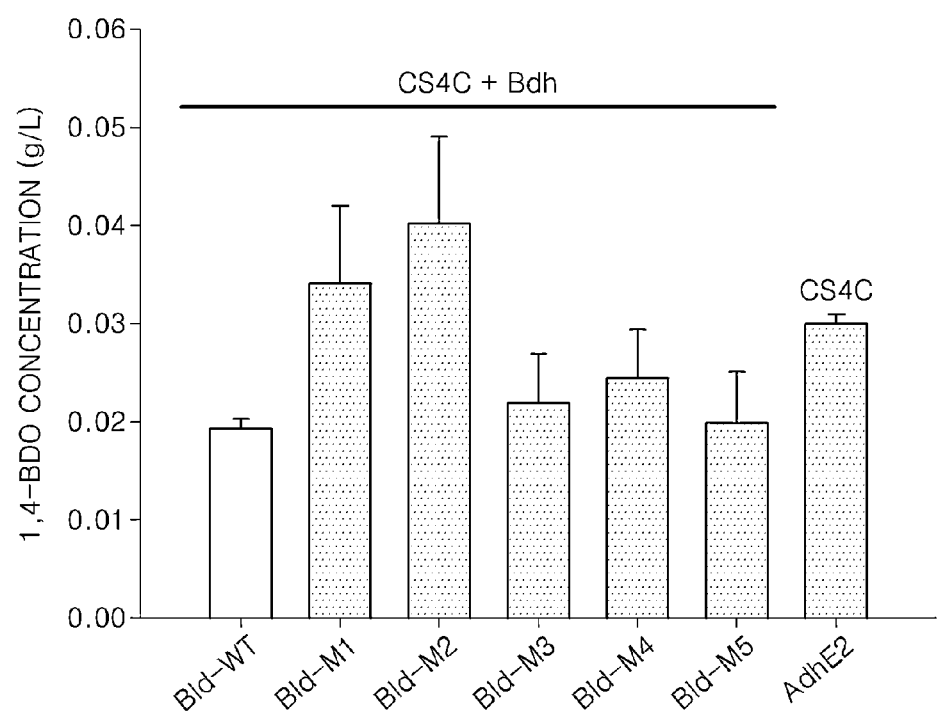
FIG. 4 is a graph showing the yield of 1,4-BDO according to a bld mutant by introducing cs4c (cat1, sucD, 4hbd, and cat2 genes) and a bdh to Bld-WT and various Bld mutants (Bld-M1 to Bld-M5) in a microorganism. As a positive control, cs4c and adhE were introduced to a microorganism and the yield of 1,4-BDO was determined.
Figure 5:
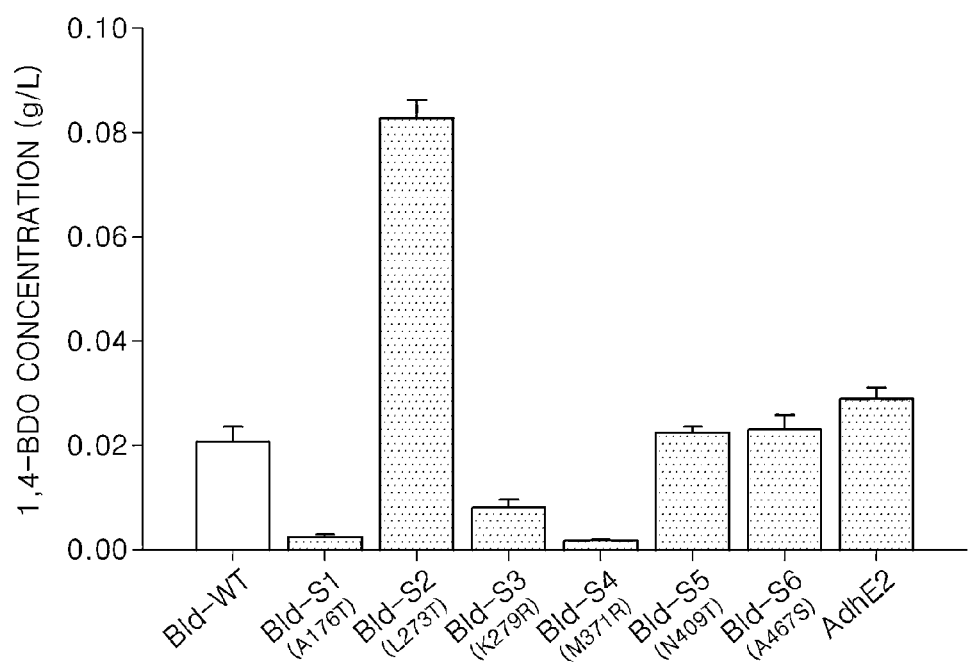
FIG. 5 is a graph of 1,4-BDO concentration for different Bld mutants, which illustrates which mutation position selected from Bld-M1 to Bld-M5 shown in Table 3 induces the most activity. Bld-S1 to Bld-S6 mutants were produced, and the yield of 1,4-BDO was confirmed by using the produced butyraldehyde dehydrogenase mutants. As a result, it was confirmed that 1,4-BDO was substantially produced in the case of Bld-S2 mutant, and a mutant having a substitution at the $273^{rd}$ position of Bld-WT (see SEQ ID NO: 1) had the greatest 1,4-BDO productivity.

As shown in Table 3 above, the Bld-M1 to Bld-M5 mutants were confirmed to have from 1 to as many as 5 mutated amino acids. Herein, in order to find out which mutant was the most effective, yields of 1,4-BDO of a total 6 mutants were measured in the same manner as Examples 4 and 5. As shown in FIG. 4, a microorganism producing the Bld-S2 (L273I) mutant was confirmed to have the highest yield of 1,4-BDO (0.08 g/L). Other mutants (Bld-S5 and Bld-S6) also showed a slight improvement. Notably, Bld-S2 having the L273I mutation showed more than three times greater effects than adhE2, which is known to have the highest performance among others of this kind.

Example 8

Confirmation of Bld Mutant Activity Via a Mutant 273

Figure 8:
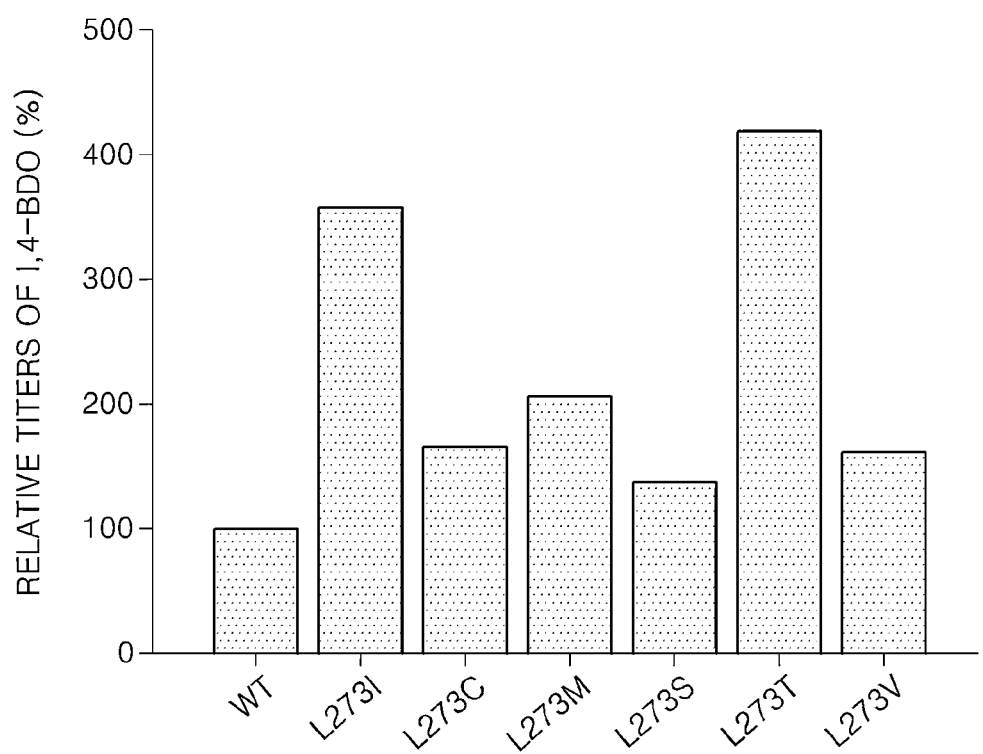
FIG. 8 is a graph displaying the activity levels of six L273X mutations, which shows relative titers of 1,4-BDO with respect to E. coli that expresses Bld-WT, such as CS4C and Bdh, and 6 mutations.

Among the bld mutants, L273I had influences on the production of 1,4-BDO. In addition, as a result of the 3D structure analysis of the bld, it was confirmed that amino acid residue 273 was a catalytic site including a binding site to NAD(P)H. Thus, in order to manufacture a mutant to make bld produce 4-hydroxybutyraldehyde in great quantities from 4-hydroxybutyryl-CoA, the amino acid residue 273 was substituted with 18 different amino acids. In comparison with a case of L273I, L273T showed high activity at the level of 15-18% (see FIG. 8). In addition, it was confirmed that 4 bld mutants, i.e., L273C, L273M, L273S, and L273V, had an activity between the activity of the wild-type bld and the activity of the L273I bld mutant. Also, other 13 mutants had reduced activities compared to the activity of the wild-type bld as shown in Tables 4 and 5 below. Table 4 shows a nucleotide sequence of a primer set used for the production of the mutant bld gene and Table 5 shows the nucleotide and amino acid change for each bld mutant.

TABLE 4

| Gene | | Sequence | SEQ ID NO: |
|---|---|---|---|
| A176T | F; | 5'-GCTAAAAAATGTGTTACCTTTGCTGTCGAA/ | 46 |
| | R; | 5'-TTCGACAGCAAAGGTAACACATTTTTTAGC | 47 |
| L273I | F; | 5'-TCTTTTGATAATAATATACCTTGTATTGCA/ | 48 |
| | R; | 5'-TGCAATACAAGGTATATTATTATCAAAAGA | 49 |
| K279R | F; | 5'-CCTTGTATTGCAGAAAGAGAAGTATTTGTT/ | 50 |
| | R; | 5'-AACAAATACTTCTCTTTCTGCAATACAAGG | 51 |
| M371R | F; | 5'-TATGACAGAACTCATGAGGCCAATATTACC/ | 52 |
| | R; | 5'-GGTAATATTGGCCTCATGAGTTCTGTCATA | 53 |
| N409T | F; | 5'-TCAAAAAATATAGACACCCTAAATAGGTTTG/ | 54 |
| | R; | 5'-CAAACCTATTTAGGGTGTCTATATTTTTTGA | 55 |
| A467S | F; | 5'-AGAAGATGTGTACTCTCCGGTTAAGCGGCC/ | 56 |
| | R; | 5'-GGCCGCTTAACCGGAGAGTACACATCTTCT | 57 |
| L273A | F; | 5'-TCTTTTGATAATAATGCGCCTTGTATTGCA/ | 58 |
| | R; | 5'-TGCAATACAAGGGCGATTATTATCAAAAGA | 59 |
| L273C | F; | 5'-TCTTTTGATAATAATTGCCCTTGTATTGCA/ | 60 |
| | R; | 5'-TGCAATACAAGGGCAATTATTATCAAAAGA | 61 |
| L273D | F; | 5'-TCTTTTGATAATAATGATCCTTGTATTGCA/ | 62 |
| | R; | 5'-TGCAATACAAGGATCATTATTATCAAAAGA | 63 |
| L273E | F; | 5'-TCTTTTGATAATAATGAACCTTGTATTGCA/ | 64 |
| | R; | 5'-TGCAATACAAGGTTCATTATTATCAAAAGA | 65 |
| L273F | F; | 5'-TCTTTTGATAATAATTTTCCTTGTATTGCA/ | 66 |
| | R; | 5'-TGCAATACAAGGAAAATTATTATCAAAAGA | 67 |
| L273G | F; | 5'-TCTTTTGATAATAATGGCCCTTGTATTGCA/ | 68 |
| | R; | 5'-TGCAATACAAGGGCCATTATTATCAAAAGA | 69 |
| L273H | F; | 5'-TCTTTTGATAATAATCATCCTTGTATTGCA/ | 70 |
| | R; | 5'-TGCAATACAAGGATGATTATTATCAAAAGA | 71 |
| L273K | F; | 5'-TCTTTTGATAATAATAAACCTTGTATTGCA/ | 72 |
| | R; | 5'-TGCAATACAAGGTTTATTATTATCAAAAGA | 73 |
| L273M | F; | 5'-TCTTTTGATAATAATATGCCTTGTATTGCA/ | 74 |
| | R; | 5'-TGCAATACAAGGCATATTATTATCAAAAGA | 75 |
| L273N | F; | 5'-TCTTTTGATAATAATAACCCTTGTATTGCA/ | 76 |
| | R; | 5'-TGCAATACAAGGGTTATTATTATCAAAAGA | 77 |
| L273P | F; | 5'-TCTTTTGATAATAATCCGCCTTGTATTGCA/ | 78 |
| | R; | 5'-TGCAATACAAGGCGGATTATTATCAAAAGA | 79 |
| L273Q | F; | 5'-TCTTTTGATAATAATCAGCCTTGTATTGCA/ | 80 |
| | R; | 5'-TGCAATACAAGGCTGATTATTATCAAAAGA | 81 |
| L273S | F; | 5'-TCTTTTGATAATAATAGCCCTTGTATTGCA/ | 82 |
| | R; | 5'-TGCAATACAAGGGCTATTATTATCAAAAGA | 83 |
| L273T | F; | 5'-TCTTTTGATAATAATACCCCTTGTATTGCA/ | 84 |
| | R; | 5'-TGCAATACAAGGGGTATTATTATCAAAAGA | 85 |

TABLE 4-continued

| Gene | | Sequence | SEQ ID NO: |
|---|---|---|---|
| L273V | F; | 5'-TCTTTTGATAATAATGTGCCTTGTATTGCA/ | 86 |
| | R; | 5'-TGCAATACAAGGCACATTATTATCAAAAGA | 87 |
| L273W | F; | 5'-TCTTTTGATAATAATTGGCCTTGTATTGCA/ | 88 |
| | R; | 5'-TGCAATACAAGGCCAATTATTATCAAAAGA | 89 |
| L273Y | F; | 5'-TCTTTTGATAATAATTATCCTTGTATTGCA/ | 90 |
| | R; | 5'-TGCAATACAAGGATAATTATTATCAAAAGA | 91 |

TABLE 5

| Bld Mutant | Nucleotide change | Amino acid change |
|---|---|---|
| L273I | TTA->ATA | L273I |
| L273A | TTA->GCG | L273A |
| L273C | TTA->TGC | L273C |
| L273D | TTA->GAT | L273D |
| L273E | TTA->GAA | L273E |
| L273F | TTA->TTT | L273F |
| L273G | TTA->GGC | L273G |
| L273H | TTA->CAT | L273H |
| L273K | TTA->AAA | L273K |
| L273M | TTA->ATG | L273M |
| L273N | TTA->AAC | L273N |
| L273P | TTA->CCG | L273P |
| L273Q | TTA->CAG | L273Q |
| L273R | TTA->CGT | L273R |
| L273S | TTA->AGC | L273S |
| L273T | TTA->ACC | L273T |
| L273V | TTA->GTG | L273V |
| L273W | TTA->TGG | L273W |
| L273Y | TTA->TAT | L273Y |

Example 9

Measurement of Enzymatic Activity of Wild-Type Bld, L273I, and L273T

Figure 9A:
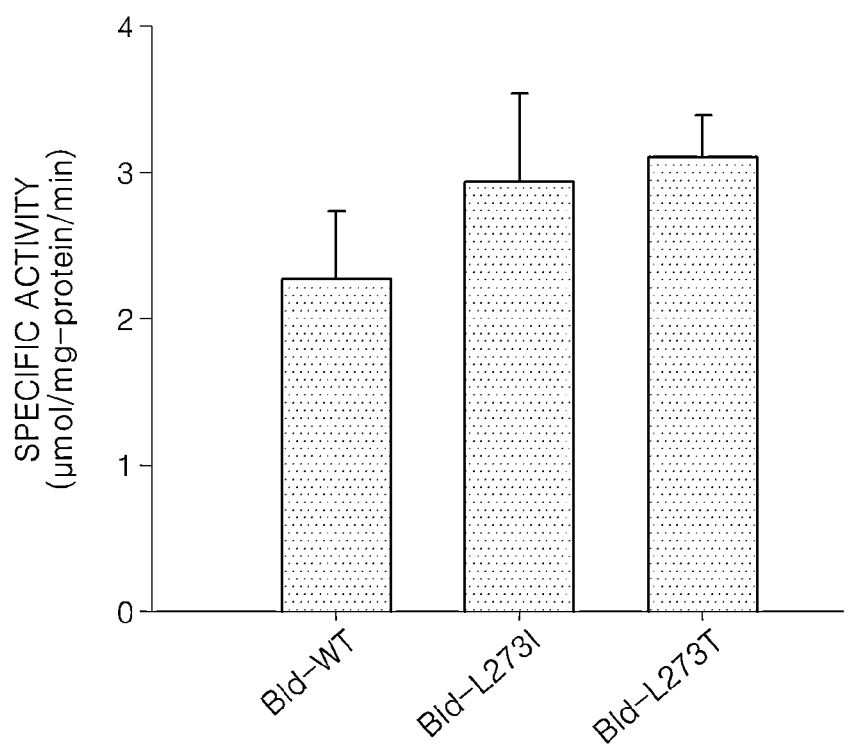
FIG. 9A is a graph displaying specific activities measured in purified Bld-WT, L273I, and L273T, by measuring concentration of NADH in a reaction mixture including butyryl-CoA as a substrate.

In order to confirm the correlation between the bld mutants and the increased 1,4-BDO productivity, butyryl-CoA was used as a substrate as to measure specific activities of purified His6-tagged wild-type bld, a L273I mutant, a L273T mutant, and AdhE2 (D'mbrosio et al., 2006). As a result, the L273I mutant and the L273T mutant each had specific activity of 2.9±0.60 and 3.1±0.30 pmol·mg$^{-1}$·min$^{-1}$. As expected, the specific activities of the mutants were 25-30% higher than that of the wild-type bld (2.3±0.46 pmol·mg$^{-1}$·min$^{-1}$) (see FIG. 9A).

Figure 9B:
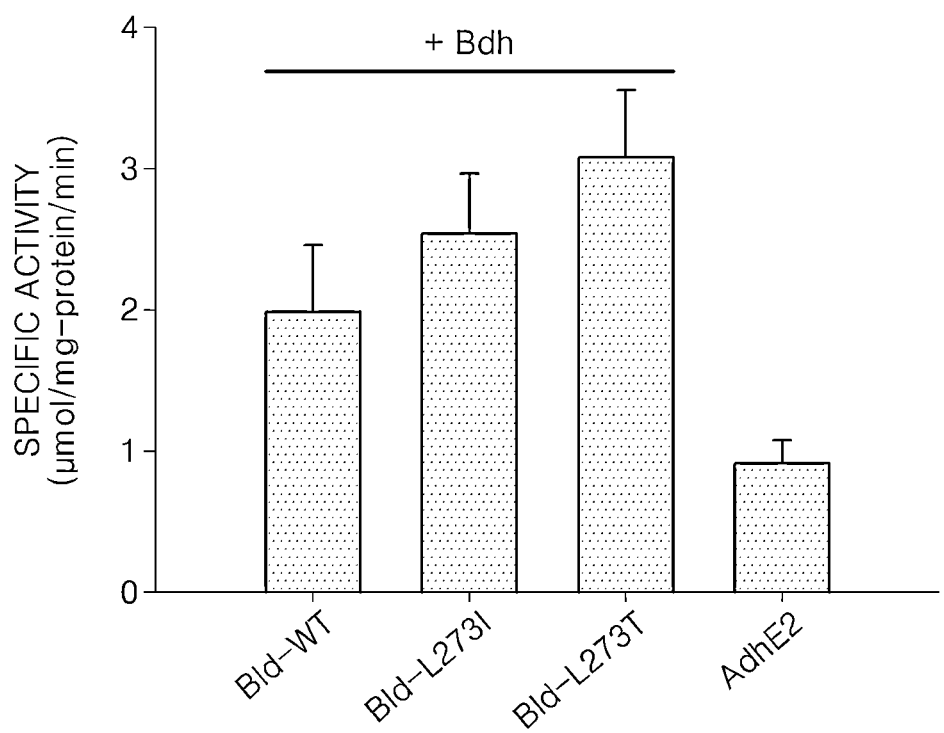
FIG. 9B is a graph displaying specific activities measured in purified Bld-WT, L273I, and L273T, by measuring concentration of NADH in a reaction mixture including purified Bdh and butyl-CoA as a substrate.

As an alternative for AdhE2 having two functions, a purified butanol dehydrogenase was added to an enzyme assay of the wild-type bld, the L273I mutant, and the L273T mutant, to evaluate butyraldehyde dehydrogenase and butanol dehydrogenase. In such a condition including butanol dehydrogenase, the specific activities of the wild-type bld, the L273I mutant, and the L273T mutant were measured 2.0±0.48, 2.5±0.44, and 3.0±0.47 pmol·mg$^{-1}$·min$^{-1}$, respectively. These specific activity measurements were about 2 to 3 times higher than the specific activity of AdhE2 (0.9±0.16 pmol·mg$^{-1}$·min$^{-1}$) (see FIG. 9B). As a result, it was confirmed that bld and bdh may replace AdhE2 in the production pathway of 1,4-BDO.

Example 10

Homology Modeling of Bld

Figure 6:
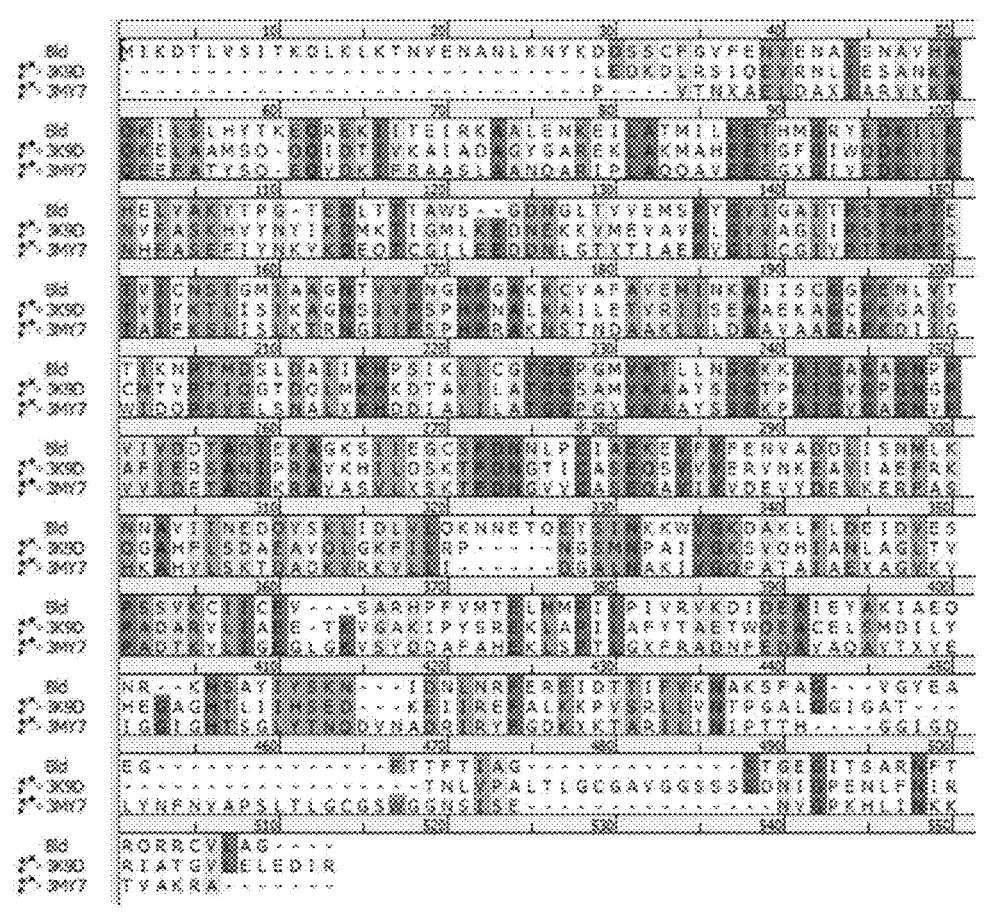
Figure 7A:
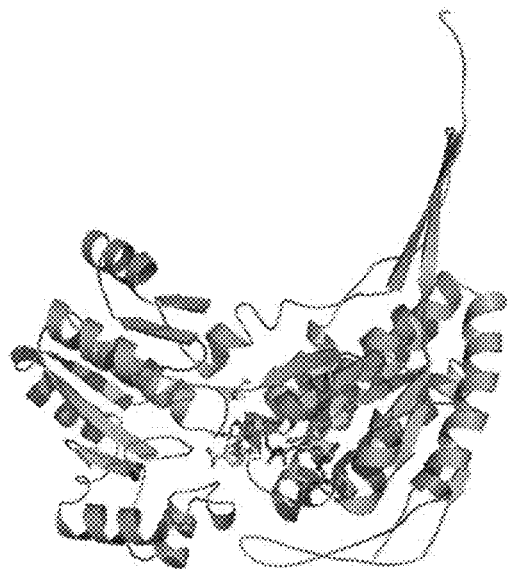
FIG. 7A is an image of the three-dimensional structure of Bld.
Figure 7B:
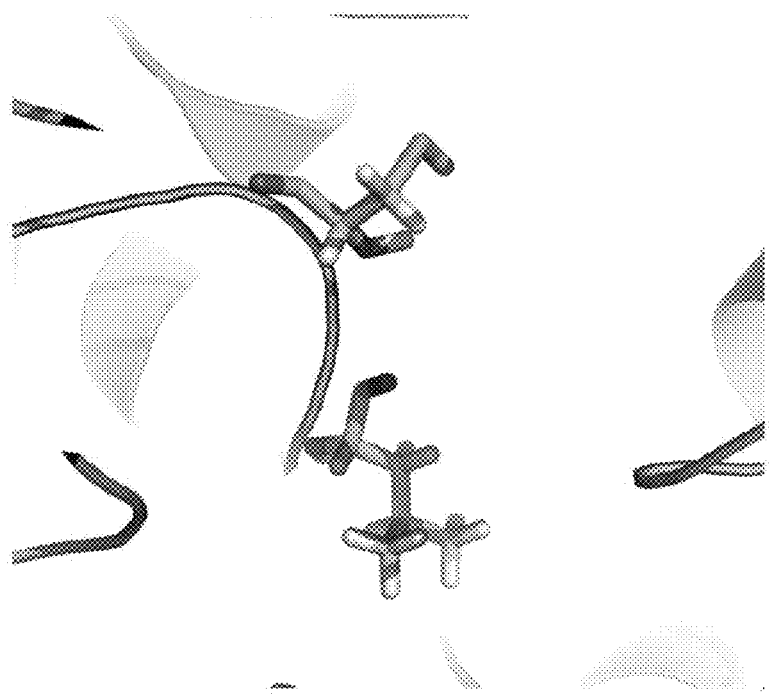
FIG. 7B is a drawing depicting the catalytic site of the Bld, and its substrate, NADPH.
Figure 7C:
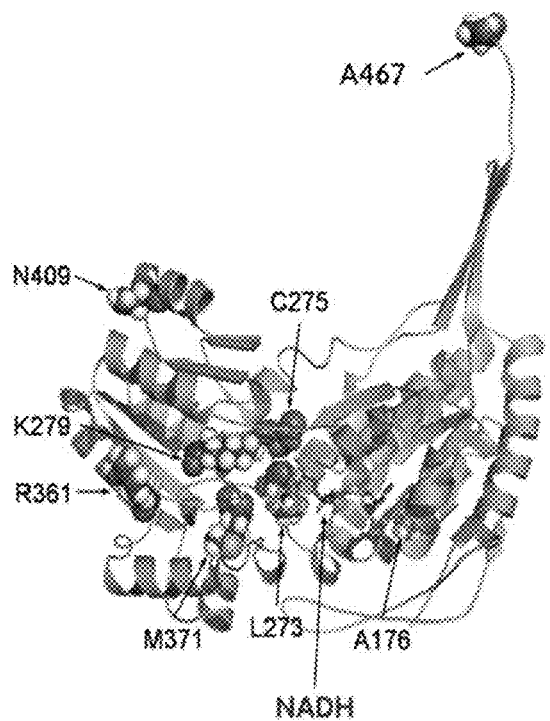
FIG. 7C is a drawing depicting the three-dimensional structure of Bld, an amino acid that affects the activity of the Bld, and NADPH as the substrate.
Figure 7D:
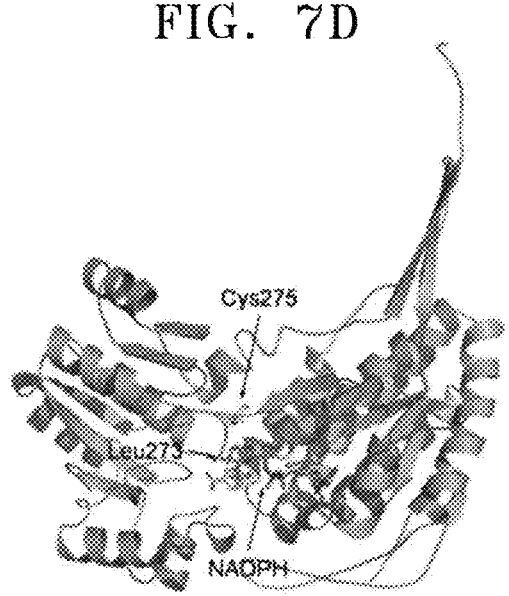
FIG. 7D is a drawing depicting the three-dimensional structure of Bld and an amino acid that affects the activity of the Bld.

Revealing the effect of mutants on an activity of an enzyme requires identification of a three-dimensional structure of the enzyme. However, the three-dimensional structure of the Bld enzyme was not identified yet. Therefore, the three-dimensional structure of the Bld was newly created by using a method of homology modeling. First, a protein structure having similar sequences with the Bld enzyme was searched for, and as a result, two proteins (Protein Data Bank ID: 3K9D, 3MY7) having the highest similarity were identified. By using the sequences of these two proteins as a template, the sequences of the Bld enzyme were arranged in this template (FIG. 6). Finally, the template-based three dimensional structure of Bld was created (FIGS. 7A and 7B). All the modeling methods used Discovery Studio 3.1 software.

According to the reaction mechanism of aldehyde dehydrogenase, a substrate that reacts with amino acids exists, and this is well preserved as cysteine amino acid in various aldehyde dehydrogenases (see, e.g., J. Mol. Biol (2007) 366, 481-493; Nat. Struct. Mol. Biol. (1997) 4, 317-326). Through the sequence alignment results, the cysteine amino acid was confirmed to be preserved in the Bld enzyme as well, which is the $275^{th}$ amino acid (Cys275) (FIG. 6). When analyzing the mutants that have an improved activity of the Bld based on the three-dimensional structure, the activity of the enzyme was shown to be increased when the mutation occurs near Cys275 or near the coenzyme binding site (FIGS. 7A and 7B). FIG. 7A shows a three-dimensional structure of the Bld enzyme which is produced by homology modeling. Cys275 and Leu273 amino acids were illustrated as yellow stick models and the coenzyme was illustrated as a pink stick model. FIG. 7B is a close-up view of the catalytic site, and the coenzyme is not shown to reveal the location of the two amino acids described above better.

From these results, possibilities for the improvement of the Bld enzyme were confirmed by mutating amino acids near Cys275. Namely, it was confirmed that the transformation of amino acids near the catalytic site that reacts with a substrate contributes to the improvement of the activity of the corresponding enzyme.

When a new enzyme according to an embodiment of the present invention is used, 1,4-BDO productivity is increased. Accordingly, when the activity of the Bld enzyme is enhanced by directed evolution, this may be very usefully utilized in industry.

According to an embodiment of the present invention, it was confirmed that *E. coli* having bld gene and bdh gene within the biosynthetic pathway of 1,4-BDO produces 1,4-BDO with high productivity. In addition, a Bld mutant protein enabling high-efficiency production of 1,4-BDO is obtained, and a recombinant microorganism having a gene encoding the mutant protein is obtained whose 1,4-BDO production concentration is improved more than twice than a parent cell. When the recombinant microorganism is used, 1,4-BDO may be efficiently produced.

It should be understood that the exemplary embodiments described therein should be considered in a descriptive sense only and not for purposes of limitation. Descriptions of features or aspects within each embodiment should typically be considered as available for other similar features or aspects in other embodiments.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein.

Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A butyraldehyde dehydrogenase (bld) mutant polypeptide, wherein the polypeptide comprises the amino acid sequence of SEQ ID NO: 2, 3, 4, 5, 6 or 7' and wherein the mutant polypeptide has butyraldehyde dehydrogenase activity".

2. A polynucleotide that encodes the bld mutant of claim 1.

3. A microorganism that produces 1,4-butanediol, the microorganism comprising the bld mutant polypeptide of claim 1.

4. The microorganism of claim 3, wherein the microorganism comprises an exogenous polynucleotide encoding the bld mutant polypeptide of claim 1.

5. The microorganism of claim 3, further comprising a butanol dehydrogenase enzyme that catalyzes the conversion of 4-hydroxybutyraldehyde into 1,4-butanediol.

6. The microorganism of claim 5, wherein the microorganism comprises a gene encoding the butanol dehydrogenase enzyme.

7. The microorganism of claim 6, wherein the butanol dehydrogenase enzyme is from *Clostridium saccharoperbutylacetonicum*.

8. The microorganism of claim 3, further comprising
   a gene encoding succinyl-CoA:coenzyme A transferase that converts succinate into succinyl-CoA,
   a gene encoding CoA-dependent succinate semialdehyde dehydrogenase that converts succinyl-CoA into succinate semialdehyde,
   a gene encoding 4-hydroxybutyrate dehydrogenase that converts succinate semialdehyde into 4-hydroxybutyrate, and
   a gene encoding 4-hydroxybutyryl-CoA:acetyl-CoA transferase that converts 4-hydroxybutyrate into 4-hydroxybutyryl-CoA.

9. The microorganism of claim 3, wherein the microorganism is *Escherichia coli*.

10. A method of producing 4-hydroxybutyaldehyde, the method comprising:
contacting 4-hydroxybutyryl-CoA with the bld mutant polypeptide of claim 1, whereby 4-hydroxybutyaldehyde is produced.

11. A method of producing 1,4-BDO, the method comprising:
contacting 4-hydroxybutyryl-CoA with the bld mutant polypeptide of claim 1; and
contacting the obtained reaction product with butanol dehydrogenase, whereby 1,4-BDO is produced.

12. A method of producing 1,4-BDO, the method comprising:
incubating a microorganism comprising a polynucleotide encoding the bld mutant of claim 1 and a polynucleotide encoding butanol dehydrogenase (bdh) with a carbon source, whereby the microorganism produces 1,4-BDO; and
separating 1,4-BDO from the incubation product.

13. The method of claim 12, further comprising introducing the polynucleotide encoding the bld mutant of claim 1 and the polynucleotide encoding butanol dehydrogenase into the microorganism prior to incubating the microorganism with a carbon source.

14. The method of claim 12, wherein the microorganism further comprises
a gene encoding succinyl-CoA:coenzyme A transferase that converts succinate into succinyl-CoA,
a gene encoding CoA-dependent succinate semialdehyde dehydrogenate that converts succinyl-CoA into succinate semialdehyde,
a gene encoding 4-hydroxybutyrate dehydrogenase that converts succinate semialdehyde into 4-hydroxybutyrate, and
a gene encoding 4-hydroxybutyryl-CoA:acetyl-CoA transferase that converts 4-hydroxybutyrate into 4-hydroxybutyryl-CoA.

15. The mutant polypeptide of claim 1, wherein the polypeptide comprises the amino acid sequence of SEQ ID NO: 2.

16. The mutant polypeptide of claim 1, wherein the polypeptide comprises amino acid sequence of SEQ ID NO: 3.

17. The mutant polypeptide of claim 1, wherein the polypeptide comprises amino acid sequence of SEQ ID NO: 4.

18. The mutant polypeptide of claim 1, wherein the polypeptide comprises amino acid sequence of SEQ ID NO: 5.

19. The mutant polypeptide of claim 1, wherein the polypeptide comprises amino acid sequence of SEQ ID NO: 6.

20. The mutant polypeptide of claim 1, wherein the polypeptide comprises amino acid sequence of SEQ ID NO: 7.

* * * * *

SEQUENCE LISTING

```
<160> NUMBER OF SEQ ID NOS: 98

<210> SEQ ID NO 1
<211> LENGTH: 468
<212> TYPE: PRT
<213> ORGANISM: Clostridium saccharoperbutylacetonicum

<400> SEQUENCE: 1

Met Ile Lys Asp Thr Leu Val Ser Ile Thr Lys Asp Leu Lys Leu Lys
1               5                   10                  15

Thr Asn Val Glu Asn Ala Asn Leu Lys Asn Tyr Lys Asp Asp Ser Ser
            20                  25                  30

Cys Phe Gly Val Phe Glu Asn Val Glu Asn Ala Ile Ser Asn Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Glu Asn Lys Glu Ile
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
    130                 135                 140

Pro Thr Glu Thr Val Ile Cys Asn Ser Ile Gly Met Ile Ala Ala Gly
145                 150                 155                 160

Asn Thr Val Val Phe Asn Gly His Pro Gly Ala Lys Lys Cys Val Ala
                165                 170                 175

Phe Ala Val Glu Met Ile Asn Lys Ala Ile Ile Ser Cys Gly Gly Pro
            180                 185                 190

Glu Asn Leu Val Thr Thr Ile Lys Asn Pro Thr Met Asp Ser Leu Asp
        195                 200                 205

Ala Ile Ile Lys His Pro Ser Ile Lys Leu Leu Cys Gly Thr Gly Gly
    210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Lys Ser Ile Ile Glu Gly Cys Ser Phe Asp Asn Asn
            260                 265                 270

Leu Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
    290                 295                 300
```

```
Glu Asp Gln Val Ser Lys Leu Ile Asp Leu Val Leu Gln Lys Asn Asn
305                 310                 315                 320

Glu Thr Gln Glu Tyr Ser Ile Asn Lys Lys Trp Val Gly Lys Asp Ala
            325                 330                 335

Lys Leu Phe Leu Asp Glu Ile Asp Val Glu Ser Pro Ser Ser Val Lys
            340                 345                 350

Cys Ile Ile Cys Glu Val Ser Ala Arg His Pro Phe Val Met Thr Glu
            355                 360                 365

Leu Met Met Pro Ile Leu Pro Ile Val Arg Val Lys Asp Ile Asp Glu
        370                 375                 380

Ala Ile Glu Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
            435                 440                 445

Gly Glu Gly Ile Thr Ser Ala Arg Asn Phe Thr Arg Gln Arg Arg Cys
450                 455                 460

Val Leu Ala Gly
465

<210> SEQ ID NO 2
<211> LENGTH: 468
<212> TYPE: PRT
<213> ORGANISM: Artificial Sequence
<220> FEATURE:
<223> OTHER INFORMATION: Synthetic (mutant of butyraldehyde
      dehydrogenase_L273I)

<400> SEQUENCE: 2

Met Ile Lys Asp Thr Leu Val Ser Ile Thr Lys Asp Leu Lys Leu Lys
1               5                   10                  15

Thr Asn Val Glu Asn Ala Asn Leu Lys Asn Tyr Lys Asp Asp Ser Ser
            20                  25                  30

Cys Phe Gly Val Phe Glu Asn Val Glu Asn Ala Ile Ser Asn Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Glu Asn Lys Glu Ile
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
    130                 135                 140

Pro Thr Glu Thr Val Ile Cys Asn Ser Ile Gly Met Ile Ala Ala Gly
145                 150                 155                 160

Asn Thr Val Val Phe Asn Gly His Pro Gly Ala Lys Lys Cys Val Ala
                165                 170                 175

Phe Ala Val Glu Met Ile Asn Lys Ala Ile Ile Ser Cys Gly Gly Pro
            180                 185                 190
```

-continued

```
Glu Asn Leu Val Thr Thr Ile Lys Asn Pro Thr Met Asp Ser Leu Asp
            195                 200                 205

Ala Ile Ile Lys His Pro Ser Ile Lys Leu Leu Cys Gly Thr Gly Gly
        210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Lys Ser Ile Ile Glu Gly Cys Ser Phe Asp Asn Asn
                260                 265                 270

Ile Pro Cys Ile Ala Glu Lys Glu Val Phe Val Phe Glu Asn Val Ala
            275                 280                 285

Asp Asp Leu Ile Ser Asn Met Leu Lys Asn Asn Ala Val Ile Ile Asn
        290                 295                 300

Glu Asp Gln Val Ser Lys Leu Ile Asp Leu Val Leu Gln Lys Asn Asn
305                 310                 315                 320

Glu Thr Gln Glu Tyr Ser Ile Asn Lys Lys Trp Val Gly Lys Asp Ala
                325                 330                 335

Lys Leu Phe Leu Asp Glu Ile Asp Val Glu Ser Pro Ser Ser Val Lys
            340                 345                 350

Cys Ile Ile Cys Glu Val Ser Ala Arg His Pro Phe Val Met Thr Glu
        355                 360                 365

Leu Met Met Pro Ile Leu Pro Ile Val Arg Val Lys Asp Ile Asp Glu
    370                 375                 380

Ala Ile Glu Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
        435                 440                 445

Gly Glu Gly Ile Thr Ser Ala Arg Asn Phe Thr Arg Gln Arg Arg Cys
    450                 455                 460

Val Leu Ala Gly
465

<210> SEQ ID NO 3
<211> LENGTH: 468
<212> TYPE: PRT
<213> ORGANISM: Artificial Sequence
<220> FEATURE:
<223> OTHER INFORMATION: Synthetic (mutant of butyraldehyde
      dehydrogenase_L273C)

<400> SEQUENCE: 3

Met Ile Lys Asp Thr Leu Val Ser Ile Thr Lys Asp Leu Lys Leu Lys
1               5                   10                  15

Thr Asn Val Glu Asn Ala Asn Leu Lys Asn Tyr Lys Asp Asp Ser Ser
            20                  25                  30

Cys Phe Gly Val Phe Glu Asn Val Glu Asn Ala Ile Ser Asn Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Glu Asn Lys Glu Ile
```

```
            65                  70                  75                  80
        Leu Ala Thr Met Ile Leu Glu Glu Thr His Met Gly Arg Tyr Glu Asp
                            85                  90                  95
        Lys Ile Leu Lys His Glu Leu Val Ala Lys Tyr Thr Pro Gly Thr Glu
                            100                 105                 110
        Asp Leu Thr Thr Thr Ala Trp Ser Gly Asp Asn Gly Leu Thr Val Val
                            115                 120                 125
        Glu Met Ser Pro Tyr Gly Val Ile Gly Ala Ile Thr Pro Ser Thr Asn
                            130                 135                 140
        Pro Thr Glu Thr Val Ile Cys Asn Ser Ile Gly Met Ile Ala Ala Gly
        145                 150                 155                 160
        Asn Thr Val Val Phe Asn Gly His Pro Gly Ala Lys Lys Cys Val Ala
                            165                 170                 175
        Phe Ala Val Glu Met Ile Asn Lys Ala Ile Ile Ser Cys Gly Gly Pro
                            180                 185                 190
        Glu Asn Leu Val Thr Thr Ile Lys Asn Pro Thr Met Asp Ser Leu Asp
                            195                 200                 205
        Ala Ile Ile Lys His Pro Ser Ile Lys Leu Leu Cys Gly Thr Gly Gly
        210                 215                 220
        Pro Gly Met Val Lys Thr Leu Leu Asn Ser Gly Lys Lys Ala Ile Gly
        225                 230                 235                 240
        Ala Gly Ala Gly Asn Pro Pro Val Ile Val Asp Asp Thr Ala Asp Ile
                            245                 250                 255
        Glu Lys Ala Gly Lys Ser Ile Ile Glu Gly Cys Ser Phe Asp Asn Asn
                            260                 265                 270
        Cys Pro Cys Ile Ala Glu Lys Glu Val Phe Val Phe Glu Asn Val Ala
                            275                 280                 285
        Asp Asp Leu Ile Ser Asn Met Leu Lys Asn Asn Ala Val Ile Ile Asn
                            290                 295                 300
        Glu Asp Gln Val Ser Lys Leu Ile Asp Leu Val Leu Gln Lys Asn Asn
        305                 310                 315                 320
        Glu Thr Gln Glu Tyr Ser Ile Asn Lys Lys Trp Val Gly Lys Asp Ala
                            325                 330                 335
        Lys Leu Phe Leu Asp Glu Ile Asp Val Glu Ser Pro Ser Ser Val Lys
                            340                 345                 350
        Cys Ile Ile Cys Glu Val Ser Ala Arg His Pro Phe Val Met Thr Glu
                            355                 360                 365
        Leu Met Met Pro Ile Leu Pro Ile Val Arg Val Lys Asp Ile Asp Glu
                            370                 375                 380
        Ala Ile Glu Tyr Ala Lys Ile Ala Glu Gln Asn Arg Lys His Ser Ala
        385                 390                 395                 400
        Tyr Ile Tyr Ser Lys Asn Ile Asp Asn Leu Asn Arg Phe Glu Arg Glu
                            405                 410                 415
        Ile Asp Thr Thr Ile Phe Val Lys Asn Ala Lys Ser Phe Ala Gly Val
                            420                 425                 430
        Gly Tyr Glu Ala Glu Gly Phe Thr Thr Phe Thr Ile Ala Gly Ser Thr
                            435                 440                 445
        Gly Glu Gly Ile Thr Ser Ala Arg Asn Phe Thr Arg Gln Arg Arg Cys
                            450                 455                 460
        Val Leu Ala Gly
        465

<210> SEQ ID NO 4
```

<211> LENGTH: 468
<212> TYPE: PRT
<213> ORGANISM: Artificial Sequence
<220> FEATURE:
<223> OTHER INFORMATION: Synthetic (mutant of butyraldehyde dehydrogenase_L273M)

<400> SEQUENCE: 4

| Met | Ile | Lys | Asp | Thr | Leu | Val | Ser | Ile | Thr | Lys | Asp | Leu | Lys | Leu | Lys |
|---|---|---|---|---|---|---|---|---|---|---|---|---|---|---|---|
| 1 | | | | 5 | | | | | 10 | | | | | 15 | |

Thr Asn Val Glu Asn Ala Asn Leu Lys Asn Tyr Lys Asp Asp Ser Ser
            20                  25                  30

Cys Phe Gly Val Phe Glu Asn Val Glu Asn Ala Ile Ser Asn Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Glu Asn Lys Glu Ile
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
    130                 135                 140

Pro Thr Glu Thr Val Ile Cys Asn Ser Ile Gly Met Ile Ala Ala Gly
145                 150                 155                 160

Asn Thr Val Val Phe Asn Gly His Pro Gly Ala Lys Lys Cys Val Ala
                165                 170                 175

Phe Ala Val Glu Met Ile Asn Lys Ala Ile Ile Ser Cys Gly Gly Pro
            180                 185                 190

Glu Asn Leu Val Thr Thr Ile Lys Asn Pro Thr Met Asp Ser Leu Asp
        195                 200                 205

Ala Ile Ile Lys His Pro Ser Ile Lys Leu Leu Cys Gly Thr Gly Gly
    210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Lys Ser Ile Ile Glu Gly Cys Ser Phe Asp Asn Asn
            260                 265                 270

Met Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
    290                 295                 300

Glu Asp Gln Val Ser Lys Leu Ile Asp Leu Val Leu Gln Lys Asn Asn
305                 310                 315                 320

Glu Thr Gln Glu Tyr Ser Ile Asn Lys Lys Trp Val Gly Lys Asp Ala
                325                 330                 335

Lys Leu Phe Leu Asp Glu Ile Asp Val Glu Ser Pro Ser Ser Val Lys
            340                 345                 350

Cys Ile Ile Cys Glu Val Ser Ala Arg His Pro Phe Val Met Thr Glu
        355                 360                 365

Leu Met Met Pro Ile Leu Pro Ile Val Arg Val Lys Asp Ile Asp Glu

```
                 370                 375                 380

Ala Ile Glu Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
                420                 425                 430

Gly Tyr Glu Ala Glu Gly Phe Thr Thr Phe Thr Ile Ala Gly Ser Thr
            435                 440                 445

Gly Glu Gly Ile Thr Ser Ala Arg Asn Phe Thr Arg Gln Arg Arg Cys
        450                 455                 460

Val Leu Ala Gly
465

<210> SEQ ID NO 5
<211> LENGTH: 468
<212> TYPE: PRT
<213> ORGANISM: Artificial Sequence
<220> FEATURE:
<223> OTHER INFORMATION: Synthetic (mutant of butyraldehyde
      dehydrogenase_L273S)

<400> SEQUENCE: 5

Met Ile Lys Asp Thr Leu Val Ser Ile Thr Lys Asp Leu Lys Leu Lys
1               5                   10                  15

Thr Asn Val Glu Asn Ala Asn Leu Lys Asn Tyr Lys Asp Asp Ser Ser
                20                  25                  30

Cys Phe Gly Val Phe Glu Asn Val Glu Asn Ala Ile Ser Asn Ala Val
            35                  40                  45

His Ala Gln Lys Ile Leu Ser Leu His Tyr Thr Lys Glu Gln Arg Glu
        50                  55                  60

Lys Ile Ile Thr Glu Ile Arg Lys Ala Ala Leu Glu Asn Lys Glu Ile
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
130                 135                 140

Pro Thr Glu Thr Val Ile Cys Asn Ser Ile Gly Met Ile Ala Ala Gly
145                 150                 155                 160

Asn Thr Val Val Phe Asn Gly His Pro Gly Ala Lys Lys Cys Val Ala
                165                 170                 175

Phe Ala Val Glu Met Ile Asn Lys Ala Ile Ser Cys Gly Gly Pro
            180                 185                 190

Glu Asn Leu Val Thr Thr Ile Lys Asn Pro Thr Met Asp Ser Leu Asp
        195                 200                 205

Ala Ile Ile Lys His Pro Ser Ile Lys Leu Leu Cys Gly Thr Gly Gly
    210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255
```

```
Glu Lys Ala Gly Lys Ser Ile Ile Glu Gly Cys Ser Phe Asp Asn Asn
                260                 265                 270

Ser Pro Cys Ile Ala Glu Lys Glu Val Phe Val Phe Glu Asn Val Ala
            275                 280                 285

Asp Asp Leu Ile Ser Asn Met Leu Lys Asn Asn Ala Val Ile Ile Asn
        290                 295                 300

Glu Asp Gln Val Ser Lys Leu Ile Asp Leu Val Leu Gln Lys Asn Asn
305                 310                 315                 320

Glu Thr Gln Glu Tyr Ser Ile Asn Lys Lys Trp Val Gly Lys Asp Ala
                325                 330                 335

Lys Leu Phe Leu Asp Glu Ile Asp Val Glu Ser Pro Ser Ser Val Lys
            340                 345                 350

Cys Ile Ile Cys Glu Val Ser Ala Arg His Pro Phe Val Met Thr Glu
        355                 360                 365

Leu Met Met Pro Ile Leu Pro Ile Val Arg Val Lys Asp Ile Asp Glu
370                 375                 380

Ala Ile Glu Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
        435                 440                 445

Gly Glu Gly Ile Thr Ser Ala Arg Asn Phe Thr Arg Gln Arg Arg Cys
450                 455                 460

Val Leu Ala Gly
465

<210> SEQ ID NO 6
<211> LENGTH: 468
<212> TYPE: PRT
<213> ORGANISM: Artificial Sequence
<220> FEATURE:
<223> OTHER INFORMATION: Synthetic (mutant of butyraldehyde
      dehydrogenase_L273T)

<400> SEQUENCE: 6

Met Ile Lys Asp Thr Leu Val Ser Ile Thr Lys Asp Leu Lys Leu Lys
1               5                   10                  15

Thr Asn Val Glu Asn Ala Asn Leu Lys Asn Tyr Lys Asp Asp Ser Ser
            20                  25                  30

Cys Phe Gly Val Phe Glu Asn Val Glu Asn Ala Ile Ser Asn Ala Val
        35                  40                  45

His Ala Gln Lys Ile Leu Ser Leu His Tyr Thr Lys Glu Gln Arg Glu
    50                  55                  60

Lys Ile Ile Thr Glu Ile Arg Lys Ala Ala Leu Glu Asn Lys Glu Ile
65                  70                  75                  80

Leu Ala Thr Met Ile Leu Glu Glu Thr His Met Gly Arg Tyr Glu Asp
                85                  90                  95

Lys Ile Leu Lys His Glu Leu Val Ala Lys Tyr Thr Pro Gly Thr Glu
            100                 105                 110

Asp Leu Thr Thr Thr Ala Trp Ser Gly Asp Asn Gly Leu Thr Val Val
        115                 120                 125

Glu Met Ser Pro Tyr Gly Val Ile Gly Ala Ile Thr Pro Ser Thr Asn
130                 135                 140
```

Pro Thr Glu Thr Val Ile Cys Asn Ser Ile Gly Met Ile Ala Ala Gly
145                 150                 155                 160

Asn Thr Val Val Phe Asn Gly His Pro Gly Ala Lys Lys Cys Val Ala
            165                 170                 175

Phe Ala Val Glu Met Ile Asn Lys Ala Ile Ile Ser Cys Gly Gly Pro
        180                 185                 190

Glu Asn Leu Val Thr Thr Ile Lys Asn Pro Thr Met Asp Ser Leu Asp
    195                 200                 205

Ala Ile Ile Lys His Pro Ser Ile Lys Leu Leu Cys Gly Thr Gly Gly
210                 215                 220

Pro Gly Met Val Lys Thr Leu Leu Asn Ser Gly Lys Lys Ala Ile Gly
225                 230                 235                 240

Ala Gly Ala Gly Asn Pro Pro Val Ile Val Asp Asp Thr Ala Asp Ile
                245                 250                 255

Glu Lys Ala Gly Lys Ser Ile Ile Glu Gly Cys Ser Phe Asp Asn Asn
            260                 265                 270

Thr Pro Cys Ile Ala Glu Lys Glu Val Phe Val Phe Glu Asn Val Ala
        275                 280                 285

Asp Asp Leu Ile Ser Asn Met Leu Lys Asn Asn Ala Val Ile Ile Asn
    290                 295                 300

Glu Asp Gln Val Ser Lys Leu Ile Asp Leu Val Leu Gln Lys Asn Asn
305                 310                 315                 320

Glu Thr Gln Glu Tyr Ser Ile Asn Lys Lys Trp Val Gly Lys Asp Ala
                325                 330                 335

Lys Leu Phe Leu Asp Glu Ile Asp Val Glu Ser Pro Ser Ser Val Lys
            340                 345                 350

Cys Ile Ile Cys Glu Val Ser Ala Arg His Pro Phe Val Met Thr Glu
        355                 360                 365

Leu Met Met Pro Ile Leu Pro Ile Val Arg Val Lys Asp Ile Asp Glu
    370                 375                 380

Ala Ile Glu Tyr Ala Lys Ile Ala Glu Gln Asn Arg Lys His Ser Ala
385                 390                 395                 400

Tyr Ile Tyr Ser Lys Asn Ile Asp Asn Leu Asn Arg Phe Glu Arg Glu
                405                 410                 415

Ile Asp Thr Thr Ile Phe Val Lys Asn Ala Lys Ser Phe Ala Gly Val
            420                 425                 430

Gly Tyr Glu Ala Glu Gly Phe Thr Thr Phe Thr Ile Ala Gly Ser Thr
        435                 440                 445

Gly Glu Gly Ile Thr Ser Ala Arg Asn Phe Thr Arg Gln Arg Arg Cys
    450                 455                 460

Val Leu Ala Gly
465

<210> SEQ ID NO 7
<211> LENGTH: 468
<212> TYPE: PRT
<213> ORGANISM: Artificial Sequence
<220> FEATURE:
<223> OTHER INFORMATION: Synthetic (mutant of butyraldehyde
      dehydrogenase_L273V)

<400> SEQUENCE: 7

Met Ile Lys Asp Thr Leu Val Ser Ile Thr Lys Asp Leu Lys Leu Lys
1               5                   10                  15

Thr Asn Val Glu Asn Ala Asn Leu Lys Asn Tyr Lys Asp Asp Ser Ser

-continued

```
             20                  25                  30
Cys Phe Gly Val Phe Glu Asn Val Glu Asn Ala Ile Ser Asn Ala Val
         35                  40                  45
His Ala Gln Lys Ile Leu Ser Leu His Tyr Thr Lys Glu Gln Arg Glu
     50                  55                  60
Lys Ile Ile Thr Glu Ile Arg Lys Ala Ala Leu Glu Asn Lys Glu Ile
 65                  70                  75                  80
Leu Ala Thr Met Ile Leu Glu Glu Thr His Met Gly Arg Tyr Glu Asp
                 85                  90                  95
Lys Ile Leu Lys His Glu Leu Val Ala Lys Tyr Thr Pro Gly Thr Glu
            100                 105                 110
Asp Leu Thr Thr Thr Ala Trp Ser Gly Asp Asn Gly Leu Thr Val Val
        115                 120                 125
Glu Met Ser Pro Tyr Gly Val Ile Gly Ala Ile Thr Pro Ser Thr Asn
    130                 135                 140
Pro Thr Glu Thr Val Ile Cys Asn Ser Ile Gly Met Ile Ala Ala Gly
145                 150                 155                 160
Asn Thr Val Val Phe Asn Gly His Pro Gly Ala Lys Lys Cys Val Ala
                165                 170                 175
Phe Ala Val Glu Met Ile Asn Lys Ala Ile Ser Cys Gly Gly Pro
            180                 185                 190
Glu Asn Leu Val Thr Thr Ile Lys Asn Pro Thr Met Asp Ser Leu Asp
        195                 200                 205
Ala Ile Ile Lys His Pro Ser Ile Lys Leu Leu Cys Gly Thr Gly Gly
    210                 215                 220
Pro Gly Met Val Lys Thr Leu Leu Asn Ser Gly Lys Lys Ala Ile Gly
225                 230                 235                 240
Ala Gly Ala Gly Asn Pro Pro Val Ile Val Asp Asp Thr Ala Asp Ile
                245                 250                 255
Glu Lys Ala Gly Lys Ser Ile Ile Glu Gly Cys Ser Phe Asp Asn Asn
            260                 265                 270
Val Pro Cys Ile Ala Glu Lys Glu Val Phe Val Phe Glu Asn Val Ala
        275                 280                 285
Asp Asp Leu Ile Ser Asn Met Leu Lys Asn Asn Ala Val Ile Ile Asn
    290                 295                 300
Glu Asp Gln Val Ser Lys Leu Ile Asp Leu Val Leu Gln Lys Asn Asn
305                 310                 315                 320
Glu Thr Gln Glu Tyr Ser Ile Asn Lys Lys Trp Val Gly Lys Asp Ala
                325                 330                 335
Lys Leu Phe Leu Asp Glu Ile Asp Val Glu Ser Pro Ser Ser Val Lys
            340                 345                 350
Cys Ile Cys Glu Val Ser Ala Arg His Pro Phe Val Met Thr Glu
        355                 360                 365
Leu Met Met Pro Ile Leu Pro Ile Val Arg Val Lys Asp Ile Asp Glu
    370                 375                 380
Ala Ile Glu Tyr Ala Lys Ile Ala Glu Gln Asn Arg Lys His Ser Ala
385                 390                 395                 400
Tyr Ile Tyr Ser Lys Asn Ile Asp Asn Leu Asn Arg Phe Glu Arg Glu
                405                 410                 415
Ile Asp Thr Thr Ile Phe Val Lys Asn Ala Lys Ser Phe Ala Gly Val
            420                 425                 430
Gly Tyr Glu Ala Glu Gly Phe Thr Thr Phe Thr Ile Ala Gly Ser Thr
        435                 440                 445
```

Gly Glu Gly Ile Thr Ser Ala Arg Asn Phe Thr Arg Gln Arg Cys
        450                 455                 460

Val Leu Ala Gly
465

<210> SEQ ID NO 8
<211> LENGTH: 382
<212> TYPE: PRT
<213> ORGANISM: Clostridium saccharoperbutylacetonicum

<400> SEQUENCE: 8

Met Glu Asn Phe Arg Phe Asn Ala Tyr Thr Glu Met Leu Phe Gly Lys
1               5                   10                  15

Gly Gln Ile Glu Lys Leu Pro Glu Val Leu Lys Arg Tyr Gly Lys Asn
            20                  25                  30

Ile Leu Leu Ala Tyr Gly Gly Ser Ile Lys Lys Asn Gly Leu Tyr
        35                  40                  45

Asp Thr Ile Gln Lys Leu Leu Asp Phe Asn Ile Val Glu Leu Ser
    50                  55                  60

Gly Ile Glu Pro Asn Pro Arg Ile Glu Thr Val Arg Arg Gly Val Glu
65                  70                  75                  80

Leu Cys Arg Lys Asn Lys Val Asp Val Ile Leu Ala Val Gly Gly Gly
                85                  90                  95

Ser Thr Ile Asp Cys Ser Lys Val Ile Gly Ala Gly Tyr Tyr Tyr Ala
            100                 105                 110

Gly Asp Ala Trp Asp Leu Val Lys Asn Pro Ala Lys Ile Gly Glu Val
        115                 120                 125

Leu Pro Ile Val Thr Val Leu Thr Met Ala Ala Thr Gly Ser Glu Met
    130                 135                 140

Asn Arg Asn Ala Val Ile Ser Lys Met Asp Thr Asn Glu Lys Leu Gly
145                 150                 155                 160

Thr Gly Ser Pro Lys Met Ile Pro Gln Thr Ser Ile Leu Asp Pro Glu
                165                 170                 175

Tyr Leu Tyr Thr Leu Pro Ala Ile Gln Thr Ala Ala Gly Cys Ala Asp
            180                 185                 190

Ile Met Ser His Ile Phe Glu Gln Tyr Phe Asn Lys Thr Thr Asp Ala
        195                 200                 205

Phe Val Gln Asp Lys Phe Ala Glu Gly Leu Leu Gln Thr Cys Ile Lys
    210                 215                 220

Tyr Cys Pro Val Ala Leu Lys Glu Pro Lys Asn Tyr Glu Ala Arg Ala
225                 230                 235                 240

Asn Ile Met Trp Ala Ser Ser Met Ala Leu Asn Gly Leu Leu Gly Ser
                245                 250                 255

Gly Lys Ala Gly Ala Trp Thr Cys His Pro Ile Glu His Glu Leu Ser
            260                 265                 270

Ala Phe Tyr Asp Ile Thr His Gly Val Gly Leu Ala Ile Leu Thr Pro
        275                 280                 285

Ser Trp Met Arg Tyr Ile Leu Ser Asp Val Thr Val Asp Lys Phe Val
    290                 295                 300

Asn Val Trp His Leu Glu Gln Lys Glu Asp Lys Phe Ala Leu Ala Asn
305                 310                 315                 320

Glu Ala Ile Asp Ala Thr Glu Lys Phe Phe Lys Ala Cys Gly Ile Pro
                325                 330                 335

Met Thr Leu Thr Glu Leu Gly Ile Asp Lys Ala Asn Phe Glu Lys Met

Ala Lys Ala Ala Val Glu His Gly Ala Leu Glu Tyr Ala Tyr Val Ser
            355                 360                 365

Leu Asn Ala Glu Asp Val Tyr Lys Ile Leu Glu Met Ser Leu
370                 375                 380

<210> SEQ ID NO 9
<211> LENGTH: 1149
<212> TYPE: DNA
<213> ORGANISM: Clostridium saccharoperbutylacetonicum

<400> SEQUENCE: 9

```
atggagaatt ttagatttaa tgcatataca gagatgcttt ttggaaaggg acaaatagag     60
aagcttccag aggttttaaa agatatggt aaaaatatat tacttgcata tggtggtgga    120
agtataaaaa agaatggact ctatgatact atccaaaagc tattgaaaga ttttaatatt    180
gttgaattaa gtggtattga accaaatcca agaattgaaa ctgtaagacg tggagttgaa    240
ctttgcagaa aaataaagt agatgttatt ttagctgttg gtgagggag tacaatagac    300
tgctcaaagg ttatagggc aggttattat tatgctggag atgcatggga ccttgtaaaa    360
aatccagcta aataggtga ggttttacca atagtgacag ttttaacaat ggcagctact    420
ggttctgaaa tgaatagaaa tgctgttatt caaagatgg atacaaatga aaagcttgga    480
acaggatcac ctaagatgat ccctcaaact tctattttag atccagaata tttgtataca    540
ttgccagcaa ttcaaacagc tgcaggttgt gctgatatta tgtcacacat atttgaacaa    600
tattttaata aaactacaga tgcttttgta caagataaat ttgcggaagg tttgttgcaa    660
acttgtataa atattgccc tgttgcttta aaggaaccaa agaattatga agctagagca    720
aatataatgt gggctagttc aatggctctt aacggacttt taggaagtgg aaagctggaa    780
gcttggactt gtcatccaat agaacatgaa ttaagtgcat tttatgatat aactcatgga    840
gtaggtcttg caatttaac tccaagttgg atgagatata tcttaagtga tgtaacagtt    900
gataagtttg ttaacgtatg catttagaa caaaagaag ataaatttgc tcttgcaaat    960
gaagcaatag atgcaacaga aaaattcttt aaagcttgtg gtattccaat gactttaact   1020
gaacttggaa tagataaagc aaactttgaa aagatggcaa agctgcagt agaacatggt   1080
gctttagaat atgcatatgt ttcattaaat gccgaggatg tatataaaat tttagaaatg   1140
tccctttaa                                                           1149
```

<210> SEQ ID NO 10
<211> LENGTH: 538
<212> TYPE: PRT
<213> ORGANISM: Clostridium kluyveri

<400> SEQUENCE: 10

Met Ser Lys Gly Ile Lys Asn Ser Gln Leu Lys Lys Lys Asn Val Lys
1               5                   10                  15

Ala Ser Asn Val Ala Glu Lys Ile Glu Glu Lys Val Glu Lys Thr Asp
                20                  25                  30

Lys Val Val Glu Lys Ala Ala Glu Val Thr Glu Lys Arg Ile Arg Asn
            35                  40                  45

Leu Lys Leu Gln Glu Lys Val Val Thr Ala Asp Val Ala Ala Asp Met
        50                  55                  60

Ile Glu Asn Gly Met Ile Val Ala Ile Ser Gly Phe Thr Pro Ser Gly
65                  70                  75                  80

-continued

Tyr Pro Lys Glu Val Pro Lys Ala Leu Thr Lys Lys Val Asn Ala Leu
             85                  90                  95
Glu Glu Glu Phe Lys Val Thr Leu Tyr Thr Gly Ser Ser Thr Gly Ala
            100                 105                 110
Asp Ile Asp Gly Glu Trp Ala Lys Ala Gly Ile Ile Glu Arg Arg Ile
            115                 120                 125
Pro Tyr Gln Thr Asn Ser Asp Met Arg Lys Lys Ile Asn Asp Gly Ser
            130                 135                 140
Ile Lys Tyr Ala Asp Met His Leu Ser His Met Ala Gln Tyr Ile Asn
145                 150                 155                 160
Tyr Ser Val Ile Pro Lys Val Asp Ile Ala Ile Glu Ala Val Ala
                165                 170                 175
Ile Thr Glu Glu Gly Asp Ile Ile Pro Ser Thr Gly Ile Gly Asn Thr
            180                 185                 190
Ala Thr Phe Val Glu Asn Ala Asp Lys Val Ile Val Glu Ile Asn Glu
            195                 200                 205
Ala Gln Pro Leu Glu Leu Glu Gly Met Ala Asp Ile Tyr Thr Leu Lys
            210                 215                 220
Asn Pro Pro Arg Arg Glu Pro Ile Pro Ile Val Asn Ala Gly Asn Arg
225                 230                 235                 240
Ile Gly Thr Thr Tyr Val Thr Cys Gly Ser Glu Lys Ile Cys Ala Ile
                245                 250                 255
Val Met Thr Asn Thr Gln Asp Lys Thr Arg Pro Leu Thr Glu Val Ser
            260                 265                 270
Pro Val Ser Gln Ala Ile Ser Asp Asn Leu Ile Gly Phe Leu Asn Lys
            275                 280                 285
Glu Val Glu Glu Gly Lys Leu Pro Lys Asn Leu Leu Pro Ile Gln Ser
            290                 295                 300
Gly Val Gly Ser Val Ala Asn Ala Val Leu Ala Gly Leu Cys Glu Ser
305                 310                 315                 320
Asn Phe Lys Asn Leu Ser Cys Tyr Thr Glu Val Ile Gln Asp Ser Met
                325                 330                 335
Leu Lys Leu Ile Lys Cys Gly Lys Ala Asp Val Val Ser Gly Thr Ser
                340                 345                 350
Ile Ser Pro Ser Pro Glu Met Leu Pro Glu Phe Ile Lys Asp Ile Asn
                355                 360                 365
Phe Phe Arg Glu Lys Ile Val Leu Arg Pro Gln Glu Ile Ser Asn Asn
            370                 375                 380
Pro Glu Ile Ala Arg Arg Ile Gly Val Ile Ser Ile Asn Thr Ala Leu
385                 390                 395                 400
Glu Val Asp Ile Tyr Gly Asn Val Asn Ser Thr His Val Met Gly Ser
                405                 410                 415
Lys Met Met Asn Gly Ile Gly Gly Ser Gly Asp Phe Ala Arg Asn Ala
                420                 425                 430
Tyr Leu Thr Ile Phe Thr Thr Glu Ser Ile Ala Lys Lys Gly Asp Ile
                435                 440                 445
Ser Ser Ile Val Pro Met Val Ser His Val Asp His Thr Glu His Asp
            450                 455                 460
Val Met Val Ile Val Thr Glu Gln Gly Val Ala Asp Leu Arg Gly Leu
465                 470                 475                 480
Ser Pro Arg Glu Lys Ala Val Ala Ile Ile Glu Asn Cys Val His Pro
                485                 490                 495
Asp Tyr Lys Asp Met Leu Met Glu Tyr Phe Glu Glu Ala Cys Lys Ser 500                 505                 510
Ser Gly Gly Asn Thr Pro His Asn Leu Glu Lys Ala Leu Ser Trp His
            515                 520                 525

Thr Lys Phe Ile Lys Thr Gly Ser Met Lys
            530                 535

<210> SEQ ID NO 11
<211> LENGTH: 1617
<212> TYPE: DNA
<213> ORGANISM: Clostridium kluyveri

<400> SEQUENCE: 11

| | |
|---|---|
| atgtctaaag gaatcaagaa tagccaattg aaaaaaaaga acgtcaaggc cagtaacgtt | 60 |
| gctgagaaga tcgaagagaa ggtggaaaag accgacaagg tcgttgagaa ggctgctgag | 120 |
| gtgaccgaaa agcgcattcg aaacttaaag ctccaggaaa aagttgtgac cgcagatgtc | 180 |
| gcagctgaca tgatcgagaa tggcatgatc gtcgcaatta gcggcttcac gccatccggg | 240 |
| tatccaaagg aggttccaaa agcccttact aagaaggtta atgcgctgga ggaggagttc | 300 |
| aaggtgacgc tgtataccgg ttctagcaca ggcgctgata ttgacggaga atgggcgaag | 360 |
| gcaggaataa tcgaacggcg tatcccatac cagaccaact ctgacatgag gaaaaaaata | 420 |
| aacgatggtt caatcaagta cgcagatatg cacctgagcc acatggctca atacattaac | 480 |
| tattctgtga ttcctaaggt tgacattgcc atcatcgagg cggtggccat taccgaggaa | 540 |
| ggggatatta ttcctagtac tggaatcggc aacacagcta cgtttgtcga aatgcggat | 600 |
| aaggtaattg tggaaataaa cgaggctcag ccgcttgagt tggaaggcat ggcagatatc | 660 |
| tataccctga gaaccctcc acgtcgcgag cccatcccga tagtcaacgc aggcaaccgc | 720 |
| atagggacca cttacgtcac ctgtggctct gaaaaaatct gcgcgatcgt catgaccaac | 780 |
| acccaagaca aaacccgccc actcaccgaa gtttctcctg tcagtcaggc aatctccgat | 840 |
| aacctgattg cttcctgaa caaagaagta gaggagggta aactcccaaa aaacctgctc | 900 |
| cccatacagt caggtgtcgg ttcggttgct aacgccgttc tagccggact ctgcgaatca | 960 |
| aacttcaaaa atttgagctg ctacacagaa gtgatccagg attcgatgtt gaagctcatc | 1020 |
| aaatgtggaa aggcagatgt ggtgtccggc acctcgatct cgccatcacc ggaaatgctg | 1080 |
| cccgagttca taaaggacat aaattttttt cgcgagaaga tagtactgcg cccccaggaa | 1140 |
| atatctaata atccggaaat agctcgtcgt ataggagtga tctccataaa cactgctttg | 1200 |
| gaagtagaca tctacggtaa tgtgaactcc acgcatgtca tgggctccaa gatgatgaac | 1260 |
| ggcatcggcg gcagcggcga cttgccgc aacgcatacc tcaccatatt cactacggag | 1320 |
| tccatcgcga agaagggcga catttcctct atcgttccta tggtttccca cgtggaccac | 1380 |
| accgagcatg acgtaatggt catcgttacc gaacaggggg ttgcggatct gcgcggtctt | 1440 |
| tccccctcgg gaaaaggccg tggcgataat tgagaattgcg tccaccccgga ttacaaggat | 1500 |
| atgctcatgg agtacttcga ggaggcttgt aagtcctcag gtggcaacac cccacacaac | 1560 |
| cttgaaaaag ccctatcctg gcacactaag ttcataaaaa ctggctcgat gaagtaa | 1617 |

<210> SEQ ID NO 12
<211> LENGTH: 451
<212> TYPE: PRT
<213> ORGANISM: Porphyromonas gingivalis

<400> SEQUENCE: 12

Met Glu Ile Lys Glu Met Val Ser Leu Ala Arg Lys Ala Gln Lys Glu

```
1               5                   10                  15
Tyr Gln Ala Thr His Asn Gln Glu Ala Val Asp Asn Ile Cys Arg Ala
            20                  25                  30
Ala Ala Lys Val Ile Tyr Glu Asn Ala Ala Ile Leu Ala Arg Glu Ala
            35                  40                  45
Val Asp Glu Thr Gly Met Gly Val Tyr Glu His Lys Val Ala Lys Asn
        50                  55                  60
Gln Gly Lys Ser Lys Gly Val Trp Tyr Asn Leu His Asn Lys Lys Ser
65                  70                  75                  80
Ile Gly Ile Leu Asn Ile Asp Glu Arg Thr Gly Met Ile Glu Ile Ala
                85                  90                  95
Lys Pro Ile Gly Val Val Gly Ala Val Thr Pro Thr Thr Asn Pro Ile
                100                 105                 110
Val Thr Pro Met Ser Asn Ile Ile Phe Ala Leu Lys Thr Cys Asn Ala
            115                 120                 125
Ile Ile Ile Ala Pro His Pro Arg Ser Lys Lys Cys Ser Ala His Ala
        130                 135                 140
Val Arg Leu Ile Lys Glu Ala Ile Ala Pro Phe Asn Val Pro Glu Gly
145                 150                 155                 160
Met Val Gln Ile Ile Glu Glu Pro Ser Ile Glu Lys Thr Gln Glu Leu
                165                 170                 175
Met Gly Ala Val Asp Val Val Ala Thr Gly Gly Met Gly Met Val
                180                 185                 190
Lys Ser Ala Tyr Ser Ser Gly Lys Pro Ser Phe Gly Val Gly Ala Gly
            195                 200                 205
Asn Val Gln Val Ile Val Asp Ser Asn Ile Asp Phe Glu Ala Ala Ala
        210                 215                 220
Glu Lys Ile Ile Thr Gly Arg Ala Phe Asp Asn Gly Ile Ile Cys Ser
225                 230                 235                 240
Gly Glu Gln Ser Ile Ile Tyr Asn Glu Ala Asp Lys Glu Ala Val Phe
                245                 250                 255
Thr Ala Phe Arg Asn His Gly Ala Tyr Phe Cys Asp Glu Ala Glu Gly
                260                 265                 270
Asp Arg Ala Arg Ala Ala Ile Phe Glu Asn Gly Ala Ile Ala Lys Asp
            275                 280                 285
Val Val Gly Gln Ser Val Ala Phe Ile Ala Lys Lys Ala Asn Ile Asn
        290                 295                 300
Ile Pro Glu Gly Thr Arg Ile Leu Val Val Glu Ala Arg Gly Val Gly
305                 310                 315                 320
Ala Glu Asp Val Ile Cys Lys Glu Lys Met Cys Pro Val Met Cys Ala
                325                 330                 335
Leu Ser Tyr Lys His Phe Glu Glu Gly Val Glu Ile Ala Arg Thr Asn
                340                 345                 350
Leu Ala Asn Glu Gly Asn Gly His Thr Cys Ala Ile His Ser Asn Asn
            355                 360                 365
Gln Ala His Ile Ile Leu Ala Gly Ser Glu Leu Thr Val Ser Arg Ile
        370                 375                 380
Val Val Asn Ala Pro Ser Ala Thr Thr Ala Gly Gly His Ile Gln Asn
385                 390                 395                 400
Gly Leu Ala Val Thr Asn Thr Leu Gly Cys Gly Ser Trp Gly Asn Asn
                405                 410                 415
Ser Ile Ser Glu Asn Phe Thr Tyr Lys His Leu Leu Asn Ile Ser Arg
                420                 425                 430
```

Ile Ala Pro Leu Asn Ser Ser Ile His Ile Pro Asp Asp Lys Glu Ile
            435                 440                 445

Trp Glu Leu
    450

<210> SEQ ID NO 13
<211> LENGTH: 1356
<212> TYPE: DNA
<213> ORGANISM: Porphyromonas gingivalis

<400> SEQUENCE: 13

```
atggagatta aagagatggt cagtcttgcg cgcaaagctc agaaggagta tcaggccacc        60
cataaccaag aagctgtgga caacatctgc cgagcagcag cgaaggttat ttacgaaaat       120
gcagcaattc tggcacgcga ggcagtggac gaaaccggca tgggtgttta cgagcacaag       180
gtggccaaga tcaaggcaa gtccaaaggt gtttggtaca acctgcataa caagaagtcg        240
attggcatcc tcaatatcga cgagcgtacc ggcatgatcg agatcgcaaa acctatcggg       300
gttgtaggcg ccgttacgcc aaccaccaac cctatcgtta ctccgatgag caacatcatc       360
tttgctctta agacctgcaa cgccatcatt atcgccccac acccgcgctc caaaaagtgc       420
tctgcccacg cagttcggct gatcaaagag ctatcgctc cgttcaacgt gcccgaaggt        480
atggttcaga tcatcgagga gcctagcatc gagaagacgc aggaattgat gggcgccgta       540
gacgtggtcg ttgctaccgg gggcatgggc atggtcaagt ctgcctactc ctcagggaag       600
ccttctttcg gtgtcggagc cggcaatgtt caggtgatag tggacagcaa catcgacttc       660
gaagcggcag cagaaaagat catcaccgga cgtgccttcg acaacggtat catctgctca       720
ggcgaacagt ccatcatcta caacgaggct gacaaggaag cagttttcac agcattccgc       780
aaccacggtg cgtactttg cgacgaggcc gagggagatc gggctcgtgc agcgatcttc        840
gaaaatggag ccatcgcgaa agatgttgtg ggccagtccg ttgccttat tgcaaagaag        900
gcgaacatta atatccccga gggtactcgt attctcgtgg tcgaagctcg cggagtaggc       960
gccgaagatg tcatctgtaa agaaaagatg tgtccagtca tgtgcgccct ctcctacaag      1020
cacttcgaag agggggtaga gatcgcaagg acgaacctcg caaacgaagg caatggccat      1080
acctgtgcta tccactccaa caaccaagca cacatcatct tggcaggctc ggagctgacc      1140
gtgtctcgca tcgtggtcaa cgcgccaagt gctaccacag caggcggtca catccagaac      1200
ggtcttgccg tcaccaatac tctaggctgc ggctcttggg gtaacaactc gatctccgaa      1260
aacttcactt ataaacacct gctcaacatt tcacgcatcg ccccgttgaa ctccagcatt      1320
catatcccag atgataagga aatctgggaa ctctaa                                1356
```

<210> SEQ ID NO 14
<211> LENGTH: 371
<212> TYPE: PRT
<213> ORGANISM: Clostridium kluyveri

<400> SEQUENCE: 14

Met Gln Leu Phe Lys Leu Lys Ser Val Thr His His Phe Asp Thr Phe
1               5                   10                  15

Ala Glu Phe Ala Lys Glu Phe Cys Leu Gly Glu Arg Asp Leu Val Ile
            20                  25                  30

Thr Asn Glu Phe Ile Tyr Glu Pro Tyr Met Lys Ala Cys Gln Leu Pro
        35                  40                  45

Cys His Phe Val Met Gln Glu Lys Tyr Gly Gln Gly Glu Pro Ser Asp

```
            50                  55                  60
Glu Met Met Asn Asn Ile Leu Ala Asp Ile Arg Asn Ile Gln Phe Asp
 65                  70                  75                  80

Arg Val Ile Gly Ile Gly Gly Thr Val Ile Asp Ile Ser Lys Leu
                 85                  90                  95

Phe Val Leu Lys Gly Leu Asn Asp Val Leu Asp Ala Phe Asp Arg Lys
                100                 105                 110

Ile Pro Leu Ile Lys Glu Lys Glu Leu Ile Ile Val Pro Thr Thr Cys
                115                 120                 125

Gly Thr Gly Ser Glu Val Thr Asn Ile Ser Ile Ala Glu Ile Lys Ser
                130                 135                 140

Arg His Thr Lys Met Gly Leu Ala Asp Asp Ala Ile Val Ala Asp His
145                 150                 155                 160

Ala Ile Ile Ile Pro Glu Leu Leu Lys Ser Leu Pro Phe His Phe Tyr
                165                 170                 175

Ala Cys Ser Ala Ile Asp Ala Leu Ile His Ala Ile Glu Ser Tyr Val
                180                 185                 190

Ser Pro Lys Ala Ser Pro Tyr Ser Arg Leu Phe Ser Glu Ala Ala Trp
                195                 200                 205

Asp Ile Ile Leu Glu Val Phe Lys Lys Ile Ala Glu His Gly Pro Glu
                210                 215                 220

Tyr Arg Phe Glu Lys Leu Gly Glu Met Ile Met Ala Ser Asn Tyr Ala
225                 230                 235                 240

Gly Ile Ala Phe Gly Asn Ala Gly Val Gly Ala Val His Ala Leu Ser
                245                 250                 255

Tyr Pro Leu Gly Gly Asn Tyr His Val Pro His Gly Glu Ala Asn Tyr
                260                 265                 270

Gln Phe Phe Thr Glu Val Phe Lys Val Tyr Gln Lys Lys Asn Pro Phe
                275                 280                 285

Gly Tyr Ile Val Glu Leu Asn Trp Lys Leu Ser Lys Ile Leu Asn Cys
                290                 295                 300

Gln Pro Glu Tyr Val Tyr Pro Lys Leu Asp Glu Leu Leu Gly Cys Leu
305                 310                 315                 320

Leu Thr Lys Lys Pro Leu His Glu Tyr Gly Met Lys Asp Glu Glu Val
                325                 330                 335

Arg Gly Phe Ala Glu Ser Val Leu Lys Thr Gln Gln Arg Leu Leu Ala
                340                 345                 350

Asn Asn Tyr Val Glu Leu Thr Val Asp Glu Ile Glu Gly Ile Tyr Arg
                355                 360                 365

Arg Leu Tyr
370

<210> SEQ ID NO 15
<211> LENGTH: 1116
<212> TYPE: DNA
<213> ORGANISM: Clostridium kluyveri

<400> SEQUENCE: 15
atgcagcttt tcaagctcaa gagcgtcaca catcactttg atacttttgc agagtttgcc      60
aaggagttct gtctcggtga acgcgacttg gtaattacca acgagttcat ctacgaaccg     120
tatatgaagg catgccagct gccttgtcat tttgtgatgc aggagaaata cggccaaggc     180
gagccttctg acgagatgat gaacaacatc ctagcagata tccgtaatat ccagttcgac     240
cgcgtgatcg ggatcggagg tggtacggtt attgacatct caaaactctt tgttctgaag     300
```

```
ggattaaatg atgttctcga cgcgttcgat cgcaagattc cccttatcaa agagaaagaa    360
ctgatcattg tgcccaccac ctgcggaacc ggctcggagg tgacgaacat ttccatcgcc    420
gagatcaagt cccggcacac caagatgggt ttggctgacg atgcaattgt tgctgaccac    480
gccataatca tccctgaact tctgaagagc ttgcccttcc acttctatgc atgctccgca    540
atcgacgctc ttattcatgc catcgagtca tacgtttctc aaaagcgtc tccatactcc     600 cgtctgttca gtgaggcggc gtgggacatt atcctgaag ttttcaagaa aatcgccgaa     660
cacggcccag agtaccgctt cgagaagctg ggggaaatga tcatggccag caactatgcc    720
ggtatcgctt tcggcaacgc aggcgttggc gccgtccacg ctctatccta cccgttgggc    780
ggcaactatc acgtgccgca tggagaagca aactatcagt tcttcaccga ggtctttaaa    840
gtataccaaa agaagaatcc gttcggctat attgtcgaac tcaactggaa gctctccaag    900
attctgaact gccagccaga gtacgtgtac ccgaagctgg atgaactgct cggttgcctt    960
cttaccaaga aacctttgca cgaatacggc atgaaggacg aagaggttcg tggcttcgcg   1020
gaatcggtcc tgaagaccca gcaacgcttg ctcgccaaca actacgtcga acttactgtc   1080
gatgagatcg aaggtatcta ccgacgtctc tactag                             1116
```

<210> SEQ ID NO 16
<211> LENGTH: 431
<212> TYPE: PRT
<213> ORGANISM: Porphyromonas gingivalis

<400> SEQUENCE: 16

```
Met Lys Asp Val Leu Ala Glu Tyr Ala Ser Arg Ile Val Ser Ala Glu
 1               5                  10                  15

Glu Ala Val Lys His Ile Lys Asn Gly Glu Arg Val Ala Leu Ser His
             20                  25                  30

Ala Ala Gly Val Pro Gln Ser Cys Val Asp Ala Leu Val Gln Gln Ala
         35                  40                  45

Asp Leu Phe Gln Asn Val Glu Ile Tyr His Met Leu Cys Leu Gly Glu
     50                  55                  60

Gly Lys Tyr Met Ala Pro Glu Met Ala Pro His Phe Arg His Ile Thr
 65                  70                  75                  80

Asn Phe Val Gly Gly Asn Ser Arg Lys Ala Val Glu Glu Asn Arg Ala
                 85                  90                  95

Asp Phe Ile Pro Val Phe Phe Tyr Glu Val Pro Ser Met Ile Arg Lys
            100                 105                 110

Asp Ile Leu His Ile Asp Val Ala Ile Val Gln Leu Ser Met Pro Asp
        115                 120                 125

Glu Asn Gly Tyr Cys Ser Phe Gly Val Ser Cys Asp Tyr Ser Lys Pro
    130                 135                 140

Ala Ala Glu Ser Ala His Leu Val Ile Gly Glu Ile Asn Arg Gln Met
145                 150                 155                 160

Pro Tyr Val His Gly Asp Asn Leu Ile His Ile Ser Lys Leu Asp Tyr
                165                 170                 175

Ile Val Met Ala Asp Tyr Pro Ile Tyr Ser Leu Ala Lys Pro Lys Ile
            180                 185                 190

Gly Glu Val Glu Glu Ala Ile Gly Arg Asn Cys Ala Glu Leu Ile Glu
        195                 200                 205

Asp Gly Ala Thr Leu Gln Leu Gly Ile Gly Ala Ile Pro Asp Ala Ala
    210                 215                 220
```

```
Leu Leu Phe Leu Lys Asp Lys Lys Asp Leu Gly Ile His Thr Glu Met
225                 230                 235                 240

Phe Ser Asp Gly Val Val Glu Leu Val Arg Ser Gly Val Ile Thr Gly
                245                 250                 255

Lys Lys Lys Thr Leu His Pro Gly Lys Met Val Ala Thr Phe Leu Met
            260                 265                 270

Gly Ser Glu Asp Val Tyr His Phe Ile Asp Lys Asn Pro Asp Val Glu
        275                 280                 285

Leu Tyr Pro Val Asp Tyr Val Asn Asp Pro Arg Val Ile Ala Gln Asn
    290                 295                 300

Asp Asn Met Val Ser Ile Asn Ser Cys Ile Glu Ile Asp Leu Met Gly
305                 310                 315                 320

Gln Val Val Ser Glu Cys Ile Gly Ser Lys Gln Phe Ser Gly Thr Gly
                325                 330                 335

Gly Gln Val Asp Tyr Val Arg Gly Ala Ala Trp Ser Lys Asn Gly Lys
            340                 345                 350

Ser Ile Met Ala Ile Pro Ser Thr Ala Lys Asn Gly Thr Ala Ser Arg
        355                 360                 365

Ile Val Pro Ile Ile Ala Glu Gly Ala Ala Val Thr Thr Leu Arg Asn
    370                 375                 380

Glu Val Asp Tyr Val Val Thr Glu Tyr Gly Ile Ala Gln Leu Lys Gly
385                 390                 395                 400

Lys Ser Leu Arg Gln Arg Ala Glu Ala Leu Ile Ala Ile Ala His Pro
                405                 410                 415

Asp Phe Arg Glu Glu Leu Thr Lys His Leu Arg Lys Arg Phe Gly
            420                 425                 430

<210> SEQ ID NO 17
<211> LENGTH: 1296
<212> TYPE: DNA
<213> ORGANISM: Porphyromonas gingivalis

<400> SEQUENCE: 17
atgaaggatg tactggcgga atacgcctcc cgcattgttt cggcggagga ggccgttaag    60
cacatcaaaa acggtgaacg ggtagctttg tcacacgctg ccggcgtgcc tcagagttgc   120
gttgacgcac tggtgcagca ggccgacctt ttccagaatg tggaaatcta tcacatgctg   180
tgcctcggtg agggtaagta tatggcgcct gagatggccc ctcacttccg ccacatcacc   240
aactttgtcg gtggtaactc ccgtaaggcg gtcgaagaaa ccgggccga tttcattccg    300 gtattctttt acgaggtgcc aagcatgatt cgcaaagaca tcctccacat tgatgtcgcc   360
atcgttcagc tttcaatgcc tgacgaaaat ggttactgtt cctttggagt atcttgcgat   420
tactccaagc cggcagcaga gagcgctcac ctggttatcg agaaatcaa ccgtcaaatg    480 ccatacgtac acggcgacaa cttgattcat atctccaagt tggattacat cgtgatggca   540
gactacccca tctactctct tgcaaagccc aagatcgggg aagtcgagga agctatcggg   600
aggaattgtg ccgagcttat tgaagatggt gccactctcc agctgggaat cggcgcgatt   660
cctgatgcgg ccctgttatt tctcaaggac aaaaaggatc tgggcatcca taccgaaatg   720
ttctccgatg gtgttgtcga attggttcgc tccggcgtta tcacaggcaa gaaaaagact   780
cttcaccccg gaagatggt cgcaaccttc ctgatgggaa gcgaggacgt gtatcatttc    840
atcgataaaa accccgatgt agaactgtat ccagtagatt acgtgaatga cccgcgtgtg   900
atcgcccaaa acgacaatat ggtctcgatt aacagctgca tcgaaatcga ccttatggga   960
```

```
caggtcgtgt ccgagtgcat cggctcaaag caattcagcg gcaccggcgg ccaagttgac      1020
tacgtgcgtg gcgcagcatg gtctaaaaac ggcaaatcga tcatggcaat cccgtccact      1080
gcaaaaaacg gtacggcatc tcgaattgta cctatcatcg cggagggcgc tgctgtcacc      1140
accctgcgca acgaggtcga ttacgttgta accgagtacg gtatcgctca gctcaagggc      1200
aagagcctgc gccagcgcgc agaggctttg atcgcgatag cccaccccga cttccgtgag      1260
gaactaacga aacatctccg caagcgattc ggataa                                1296
```

<210> SEQ ID NO 18
<211> LENGTH: 44
<212> TYPE: DNA
<213> ORGANISM: Artificial Sequence
<220> FEATURE:
<223> OTHER INFORMATION: Synthetic (forward primer of bdh)

<400> SEQUENCE: 18

```
gctctagaag gaggattaca aaatggagaa ttttagattt aatg                         44
```

<210> SEQ ID NO 19
<211> LENGTH: 33
<212> TYPE: DNA
<213> ORGANISM: Artificial Sequence
<220> FEATURE:
<223> OTHER INFORMATION: Synthetic (reverse primer of bdh)

<400> SEQUENCE: 19

```
ttcccttgcg gccgcttaaa gggacatttc taa                                     33
```

<210> SEQ ID NO 20
<211> LENGTH: 45
<212> TYPE: DNA
<213> ORGANISM: Artificial Sequence
<220> FEATURE:
<223> OTHER INFORMATION: Synthetic (forward primer of bld)

<400> SEQUENCE: 20

```
gccccgggag gaggattaca aaatgattaa agacacgcta gtttc                        45
```

<210> SEQ ID NO 21
<211> LENGTH: 35
<212> TYPE: DNA
<213> ORGANISM: Artificial Sequence
<220> FEATURE:
<223> OTHER INFORMATION: Synthetic (reverse primer of bld)

<400> SEQUENCE: 21

```
ttcccttgcg gccgcttaac cggcgagtac acatc                                   35
```

<210> SEQ ID NO 22
<211> LENGTH: 43
<212> TYPE: DNA
<213> ORGANISM: Artificial Sequence
<220> FEATURE:
<223> OTHER INFORMATION: Synthetic (forward primer of cs4c)

<400> SEQUENCE: 22

```
gctctagaag gaggattaca aaatgagtaa agggattaag aac                          43
```

<210> SEQ ID NO 23
<211> LENGTH: 33
<212> TYPE: DNA
<213> ORGANISM: Artificial Sequence
<220> FEATURE:
<223> OTHER INFORMATION: Synthetic (reverse primer of cs4c)

```
<400> SEQUENCE: 23
ttcccttgcg gccgcttaac caaaacgttt gcg                                    33

<210> SEQ ID NO 24
<211> LENGTH: 23
<212> TYPE: DNA
<213> ORGANISM: Artificial Sequence
<220> FEATURE:
<223> OTHER INFORMATION: Synthetic (Sub_BamHI_R)

<400> SEQUENCE: 24
cgggatcccg gtgtgaaata ccg                                              23

<210> SEQ ID NO 25
<211> LENGTH: 23
<212> TYPE: DNA
<213> ORGANISM: Artificial Sequence
<220> FEATURE:
<223> OTHER INFORMATION: Synthetic (Sub_EcoRI_R)

<400> SEQUENCE: 25
cgggatcccg gtgtgaaata ccg                                              23

<210> SEQ ID NO 26
<211> LENGTH: 20
<212> TYPE: DNA
<213> ORGANISM: Artificial Sequence
<220> FEATURE:
<223> OTHER INFORMATION: Synthetic (Sub_SacI_F)

<400> SEQUENCE: 26
gagctcccga ctggaaagcg                                                  20

<210> SEQ ID NO 27
<211> LENGTH: 24
<212> TYPE: DNA
<213> ORGANISM: Artificial Sequence
<220> FEATURE:
<223> OTHER INFORMATION: Synthetic (Sub_SalI_F)

<400> SEQUENCE: 27
acgcgtcgac ccgactggaa agcg                                             24

<210> SEQ ID NO 28
<211> LENGTH: 40
<212> TYPE: DNA
<213> ORGANISM: Artificial Sequence
<220> FEATURE:
<223> OTHER INFORMATION: Synthetic (forward primer of adhE2)

<400> SEQUENCE: 28
gctctagaag gaggattaca aaatgatttt gcatctgctg                            40

<210> SEQ ID NO 29
<211> LENGTH: 36
<212> TYPE: DNA
<213> ORGANISM: Artificial Sequence
<220> FEATURE:
<223> OTHER INFORMATION: Synthetic (reverse primer of adhE2)

<400> SEQUENCE: 29
ttcccttgcg gccgcttaaa acgacttgat gtagat                                36

<210> SEQ ID NO 30
```

```
<210> SEQ ID NO 30
<211> LENGTH: 45
<212> TYPE: DNA
<213> ORGANISM: Artificial Sequence
<220> FEATURE:
<223> OTHER INFORMATION: Synthetic (forward primer of adh1)

<400> SEQUENCE: 30
gctctagaag gaggattaca aaatgatgag atttacatta ccaag            45

<210> SEQ ID NO 31
<211> LENGTH: 36
<212> TYPE: DNA
<213> ORGANISM: Artificial Sequence
<220> FEATURE:
<223> OTHER INFORMATION: Synthetic (reverse primer of adh1)

<400> SEQUENCE: 31
ttcccttgcg gccgcttaaa aatcaacttc tgtacc                      36

<210> SEQ ID NO 32
<211> LENGTH: 43
<212> TYPE: DNA
<213> ORGANISM: Artificial Sequence
<220> FEATURE:
<223> OTHER INFORMATION: Synthetic (forward primer of adhE1)

<400> SEQUENCE: 32
gctctagaag gaggattaca aaatgaaagt cacaacagta aag              43

<210> SEQ ID NO 33
<211> LENGTH: 35
<212> TYPE: DNA
<213> ORGANISM: Artificial Sequence
<220> FEATURE:
<223> OTHER INFORMATION: Synthetic (reverse primer of adhE1)

<400> SEQUENCE: 33
ttcccttgcg gccgcttaag gttgtttttt aaaac                       35

<210> SEQ ID NO 34
<211> LENGTH: 40
<212> TYPE: DNA
<213> ORGANISM: Artificial Sequence
<220> FEATURE:
<223> OTHER INFORMATION: Synthetic (forward primer of adhE2)

<400> SEQUENCE: 34
gctctagaag gaggattaca aaatgatttt gcatctgctg                  40

<210> SEQ ID NO 35
<211> LENGTH: 36
<212> TYPE: DNA
<213> ORGANISM: Artificial Sequence
<220> FEATURE:
<223> OTHER INFORMATION: Synthetic (reverse primer of adhE2)

<400> SEQUENCE: 35
ttcccttgcg gccgcttaaa acgacttgat gtagat                      36

<210> SEQ ID NO 36
<211> LENGTH: 43
<212> TYPE: DNA
<213> ORGANISM: Artificial Sequence
<220> FEATURE:
<223> OTHER INFORMATION: Synthetic (forward primer of bdhA)

<400> SEQUENCE: 36
```
gctctagaag gaggattaca aaatgctaag ttttgattat tca                43

<210> SEQ ID NO 37
<211> LENGTH: 38
<212> TYPE: DNA
<213> ORGANISM: Artificial Sequence
<220> FEATURE:
<223> OTHER INFORMATION: Synthetic (reverse primer of bdhA)

<400> SEQUENCE: 37
ttcccttgcg gccgcttata agatttttta aatatctc                      38

<210> SEQ ID NO 38
<211> LENGTH: 47
<212> TYPE: DNA
<213> ORGANISM: Artificial Sequence
<220> FEATURE:
<223> OTHER INFORMATION: Synthetic (forward primer of bdhB)

<400> SEQUENCE: 38
gccccgggag gaggattaca aaatggttga tttcgaatat tcaatac            47

<210> SEQ ID NO 39
<211> LENGTH: 39
<212> TYPE: DNA
<213> ORGANISM: Artificial Sequence
<220> FEATURE:
<223> OTHER INFORMATION: Synthetic (reverse primer of bdhB)

<400> SEQUENCE: 39
ttcccttgcg gccgcttaca cagatttttt gaatatttg                     39

<210> SEQ ID NO 40
<211> LENGTH: 31
<212> TYPE: DNA
<213> ORGANISM: Artificial Sequence
<220> FEATURE:
<223> OTHER INFORMATION: Synthetic (forward primer of bld (pET21a))

<400> SEQUENCE: 40
gcgaattcat gattaaagac acgctagttt c                             31

<210> SEQ ID NO 41
<211> LENGTH: 28
<212> TYPE: DNA
<213> ORGANISM: Artificial Sequence
<220> FEATURE:
<223> OTHER INFORMATION: Synthetic (reverse primer of bld (pET21a))

<400> SEQUENCE: 41
aaaactcgag accggcgagt acacatct                                 28

<210> SEQ ID NO 42
<211> LENGTH: 29
<212> TYPE: DNA
<213> ORGANISM: Artificial Sequence
<220> FEATURE:
<223> OTHER INFORMATION: Synthetic (forward primer of adhE2 (pET21a))

<400> SEQUENCE: 42
gcggatccat gattttgcat ctgctgcga                                29

<210> SEQ ID NO 43
<211> LENGTH: 32
<212> TYPE: DNA

<213> ORGANISM: Artificial Sequence
<220> FEATURE:
<223> OTHER INFORMATION: Synthetic (reverse primer of adhE2 (pET21a))

<400> SEQUENCE: 43
aaaactcgag aaacgacttg atgtagatat cc                             32

<210> SEQ ID NO 44
<211> LENGTH: 29
<212> TYPE: DNA
<213> ORGANISM: Artificial Sequence
<220> FEATURE:
<223> OTHER INFORMATION: Synthetic (forward primer of bdh (pET21a))

<400> SEQUENCE: 44
gcgaattcat ggagaatttt agatttaat                                 29

<210> SEQ ID NO 45
<211> LENGTH: 34
<212> TYPE: DNA
<213> ORGANISM: Artificial Sequence
<220> FEATURE:
<223> OTHER INFORMATION: Synthetic (reverse primer of bdh (pET21a))

<400> SEQUENCE: 45
aaaactcgag aagggacatt tctaaaattt tata                           34

<210> SEQ ID NO 46
<211> LENGTH: 30
<212> TYPE: DNA
<213> ORGANISM: Artificial Sequence
<220> FEATURE:
<223> OTHER INFORMATION: Synthetic (forward primer for A176T)

<400> SEQUENCE: 46
gctaaaaaat gtgttaccttt tgctgtcgaa                               30

<210> SEQ ID NO 47
<211> LENGTH: 30
<212> TYPE: DNA
<213> ORGANISM: Artificial Sequence
<220> FEATURE:
<223> OTHER INFORMATION: Synthetic (reverse primer for A176T)

<400> SEQUENCE: 47
ttcgacagca aaggtaacac attttttagc                                30

<210> SEQ ID NO 48
<211> LENGTH: 30
<212> TYPE: DNA
<213> ORGANISM: Artificial Sequence
<220> FEATURE:
<223> OTHER INFORMATION: Synthetic (forward primer for L273I)

<400> SEQUENCE: 48
tcttttgata taatatacc ttgtattgca                                 30

<210> SEQ ID NO 49
<211> LENGTH: 30
<212> TYPE: DNA
<213> ORGANISM: Artificial Sequence
<220> FEATURE:
<223> OTHER INFORMATION: Synthetic (reverse primer for L273I)

<400> SEQUENCE: 49
tgcaatacaa ggtatattat tatcaaaaga                                30

<210> SEQ ID NO 50
<211> LENGTH: 30
<212> TYPE: DNA
<213> ORGANISM: Artificial Sequence
<220> FEATURE:
<223> OTHER INFORMATION: Synthetic (forward primer for K279R)

<400> SEQUENCE: 50
ccttgtattg cagaaagaga agtatttgtt                                    30

<210> SEQ ID NO 51
<211> LENGTH: 30
<212> TYPE: DNA
<213> ORGANISM: Artificial Sequence
<220> FEATURE:
<223> OTHER INFORMATION: Synthetic (reverse primer for K279R)

<400> SEQUENCE: 51
aacaaatact tctctttctg caatacaagg                                    30

<210> SEQ ID NO 52
<211> LENGTH: 30
<212> TYPE: DNA
<213> ORGANISM: Artificial Sequence
<220> FEATURE:
<223> OTHER INFORMATION: Synthetic (forward primer for M371R)

<400> SEQUENCE: 52
tatgacagaa ctcatgaggc caatattacc                                    30

<210> SEQ ID NO 53
<211> LENGTH: 30
<212> TYPE: DNA
<213> ORGANISM: Artificial Sequence
<220> FEATURE:
<223> OTHER INFORMATION: Synthetic (reverse primer for M371R)

<400> SEQUENCE: 53
ggtaatattg gcctcatgag ttctgtcata                                    30

<210> SEQ ID NO 54
<211> LENGTH: 31
<212> TYPE: DNA
<213> ORGANISM: Artificial Sequence
<220> FEATURE:
<223> OTHER INFORMATION: Synthetic (forward primer for N409T)

<400> SEQUENCE: 54
tcaaaaaata tagacaccct aaataggttt g                                  31

<210> SEQ ID NO 55
<211> LENGTH: 31
<212> TYPE: DNA
<213> ORGANISM: Artificial Sequence
<220> FEATURE:
<223> OTHER INFORMATION: Synthetic (reverse primer for N409T)

<400> SEQUENCE: 55
caaacctatt tagggtgtct atattttttg a                                  31

<210> SEQ ID NO 56
<211> LENGTH: 30
<212> TYPE: DNA
<213> ORGANISM: Artificial Sequence
<220> FEATURE:

<223> OTHER INFORMATION: Synthetic (forward primer for A467S)

<400> SEQUENCE: 56
agaagatgtg tactctccgg ttaagcggcc                                30

<210> SEQ ID NO 57
<211> LENGTH: 30
<212> TYPE: DNA
<213> ORGANISM: Artificial Sequence
<220> FEATURE:
<223> OTHER INFORMATION: Synthetic (reverse primer for A467S)

<400> SEQUENCE: 57
ggccgcttaa ccggagagta cacatcttct                                30

<210> SEQ ID NO 58
<211> LENGTH: 30
<212> TYPE: DNA
<213> ORGANISM: Artificial Sequence
<220> FEATURE:
<223> OTHER INFORMATION: Synthetic (forward primer for L273A)

<400> SEQUENCE: 58
tcttttgata ataatgcgcc ttgtattgca                                30

<210> SEQ ID NO 59
<211> LENGTH: 30
<212> TYPE: DNA
<213> ORGANISM: Artificial Sequence
<220> FEATURE:
<223> OTHER INFORMATION: Synthetic (reverse primer for L273A)

<400> SEQUENCE: 59
tgcaatacaa gggcgattat tatcaaaaga                                30

<210> SEQ ID NO 60
<211> LENGTH: 30
<212> TYPE: DNA
<213> ORGANISM: Artificial Sequence
<220> FEATURE:
<223> OTHER INFORMATION: Synthetic (forward primer for L273C)

<400> SEQUENCE: 60
tcttttgata ataattgccc ttgtattgca                                30

<210> SEQ ID NO 61
<211> LENGTH: 30
<212> TYPE: DNA
<213> ORGANISM: Artificial Sequence
<220> FEATURE:
<223> OTHER INFORMATION: Synthetic (reverse primer for L273C)

<400> SEQUENCE: 61
tgcaatacaa gggcaattat tatcaaaaga                                30

<210> SEQ ID NO 62
<211> LENGTH: 30
<212> TYPE: DNA
<213> ORGANISM: Artificial Sequence
<220> FEATURE:
<223> OTHER INFORMATION: Synthetic (forward primer for L273D)

<400> SEQUENCE: 62
tcttttgata ataatgatcc ttgtattgca                                30

<210> SEQ ID NO 63
<211> LENGTH: 30
<212> TYPE: DNA
<213> ORGANISM: Artificial Sequence
<220> FEATURE:
<223> OTHER INFORMATION: Synthetic (reverse primer for L273D)

<400> SEQUENCE: 63
tgcaatacaa ggatcattat tatcaaaaga                                30

<210> SEQ ID NO 64
<211> LENGTH: 30
<212> TYPE: DNA
<213> ORGANISM: Artificial Sequence
<220> FEATURE:
<223> OTHER INFORMATION: Synthetic (forward primer for L273E)

<400> SEQUENCE: 64
tcttttgata ataatgaacc ttgtattgca                                30

<210> SEQ ID NO 65
<211> LENGTH: 30
<212> TYPE: DNA
<213> ORGANISM: Artificial Sequence
<220> FEATURE:
<223> OTHER INFORMATION: Synthetic (reverse primer for L273E)

<400> SEQUENCE: 65
tgcaatacaa ggttcattat tatcaaaaga                                30

<210> SEQ ID NO 66
<211> LENGTH: 30
<212> TYPE: DNA
<213> ORGANISM: Artificial Sequence
<220> FEATURE:
<223> OTHER INFORMATION: Synthetic (forward primer for L273F)

<400> SEQUENCE: 66
tcttttgata ataattttcc ttgtattgca                                30

<210> SEQ ID NO 67
<211> LENGTH: 30
<212> TYPE: DNA
<213> ORGANISM: Artificial Sequence
<220> FEATURE:
<223> OTHER INFORMATION: Synthetic (reverse primer for L273F)

<400> SEQUENCE: 67
tgcaatacaa ggaaaattat tatcaaaaga                                30

<210> SEQ ID NO 68
<211> LENGTH: 30
<212> TYPE: DNA
<213> ORGANISM: Artificial Sequence
<220> FEATURE:
<223> OTHER INFORMATION: Synthetic (forward primer for L273G)

<400> SEQUENCE: 68
tcttttgata ataatggccc ttgtattgca                                30

<210> SEQ ID NO 69
<211> LENGTH: 30
<212> TYPE: DNA
<213> ORGANISM: Artificial Sequence
<220> FEATURE:
<223> OTHER INFORMATION: Synthetic (reverse primer for L273G)

```
<400> SEQUENCE: 69
tgcaatacaa gggccattat tatcaaaaga                                    30

<210> SEQ ID NO 70
<211> LENGTH: 30
<212> TYPE: DNA
<213> ORGANISM: Artificial Sequence
<220> FEATURE:
<223> OTHER INFORMATION: Synthetic (forward primer for L273H)

<400> SEQUENCE: 70
tcttttgata ataatcatcc ttgtattgca                                    30

<210> SEQ ID NO 71
<211> LENGTH: 30
<212> TYPE: DNA
<213> ORGANISM: Artificial Sequence
<220> FEATURE:
<223> OTHER INFORMATION: Synthetic (reverse primer for L273H)

<400> SEQUENCE: 71
tgcaatacaa ggatgattat tatcaaaaga                                    30

<210> SEQ ID NO 72
<211> LENGTH: 30
<212> TYPE: DNA
<213> ORGANISM: Artificial Sequence
<220> FEATURE:
<223> OTHER INFORMATION: Synthetic (forward primer for L273K)

<400> SEQUENCE: 72
tcttttgata ataataaacc ttgtattgca                                    30

<210> SEQ ID NO 73
<211> LENGTH: 30
<212> TYPE: DNA
<213> ORGANISM: Artificial Sequence
<220> FEATURE:
<223> OTHER INFORMATION: Synthetic (reverse primer for L273K)

<400> SEQUENCE: 73
tgcaatacaa ggtttattat tatcaaaaga                                    30

<210> SEQ ID NO 74
<211> LENGTH: 30
<212> TYPE: DNA
<213> ORGANISM: Artificial Sequence
<220> FEATURE:
<223> OTHER INFORMATION: Synthetic (forward primer for L273M)

<400> SEQUENCE: 74
tcttttgata ataatatgcc ttgtattgca                                    30

<210> SEQ ID NO 75
<211> LENGTH: 30
<212> TYPE: DNA
<213> ORGANISM: Artificial Sequence
<220> FEATURE:
<223> OTHER INFORMATION: Synthetic (reverse primer for L273M)

<400> SEQUENCE: 75
tgcaatacaa ggcatattat tatcaaaaga                                    30

<210> SEQ ID NO 76
<211> LENGTH: 30
```

```
<212> TYPE: DNA
<213> ORGANISM: Artificial Sequence
<220> FEATURE:
<223> OTHER INFORMATION: Synthetic (forward primer for L273N)

<400> SEQUENCE: 76
tcttttgata ataataaccc ttgtattgca                                    30

<210> SEQ ID NO 77
<211> LENGTH: 30
<212> TYPE: DNA
<213> ORGANISM: Artificial Sequence
<220> FEATURE:
<223> OTHER INFORMATION: Synthetic (reverse primer for L273N)

<400> SEQUENCE: 77
tgcaatacaa gggttattat tatcaaaaga                                    30

<210> SEQ ID NO 78
<211> LENGTH: 30
<212> TYPE: DNA
<213> ORGANISM: Artificial Sequence
<220> FEATURE:
<223> OTHER INFORMATION: Synthetic (forward primer for L273P)

<400> SEQUENCE: 78
tcttttgata ataatccgcc ttgtattgca                                    30

<210> SEQ ID NO 79
<211> LENGTH: 30
<212> TYPE: DNA
<213> ORGANISM: Artificial Sequence
<220> FEATURE:
<223> OTHER INFORMATION: Synthetic (reverse primer for L273P)

<400> SEQUENCE: 79
tgcaatacaa ggcggattat tatcaaaaga                                    30

<210> SEQ ID NO 80
<211> LENGTH: 30
<212> TYPE: DNA
<213> ORGANISM: Artificial Sequence
<220> FEATURE:
<223> OTHER INFORMATION: Synthetic (forward primer for L273Q)

<400> SEQUENCE: 80
tcttttgata ataatcagcc ttgtattgca                                    30

<210> SEQ ID NO 81
<211> LENGTH: 30
<212> TYPE: DNA
<213> ORGANISM: Artificial Sequence
<220> FEATURE:
<223> OTHER INFORMATION: Synthetic (reverse primer for L273Q)

<400> SEQUENCE: 81
tgcaatacaa ggctgattat tatcaaaaga                                    30

<210> SEQ ID NO 82
<211> LENGTH: 30
<212> TYPE: DNA
<213> ORGANISM: Artificial Sequence
<220> FEATURE:
<223> OTHER INFORMATION: Synthetic (forward primer for L273S)

<400> SEQUENCE: 82
```

-continued tcttttgata ataatagccc ttgtattgca                                    30

<210> SEQ ID NO 83
<211> LENGTH: 30
<212> TYPE: DNA
<213> ORGANISM: Artificial Sequence
<220> FEATURE:
<223> OTHER INFORMATION: Synthetic (reverse primer for L273S)

<400> SEQUENCE: 83
tgcaatacaa gggctattat tatcaaaaga                                    30

<210> SEQ ID NO 84
<211> LENGTH: 30
<212> TYPE: DNA
<213> ORGANISM: Artificial Sequence
<220> FEATURE:
<223> OTHER INFORMATION: Synthetic (forward primer for L273T)

<400> SEQUENCE: 84
tcttttgata ataataccccc ttgtattgca                                   30

<210> SEQ ID NO 85
<211> LENGTH: 30
<212> TYPE: DNA
<213> ORGANISM: Artificial Sequence
<220> FEATURE:
<223> OTHER INFORMATION: Synthetic (reverse primer for L273T)

<400> SEQUENCE: 85
tgcaatacaa ggggtattat tatcaaaaga                                    30

<210> SEQ ID NO 86
<211> LENGTH: 30
<212> TYPE: DNA
<213> ORGANISM: Artificial Sequence
<220> FEATURE:
<223> OTHER INFORMATION: Synthetic (forward primer for L273V)

<400> SEQUENCE: 86
tcttttgata ataatgtgcc ttgtattgca                                    30

<210> SEQ ID NO 87
<211> LENGTH: 30
<212> TYPE: DNA
<213> ORGANISM: Artificial Sequence
<220> FEATURE:
<223> OTHER INFORMATION: Synthetic (reverse primer for L273V)

<400> SEQUENCE: 87
tgcaatacaa ggcacattat tatcaaaaga                                    30

<210> SEQ ID NO 88
<211> LENGTH: 30
<212> TYPE: DNA
<213> ORGANISM: Artificial Sequence
<220> FEATURE:
<223> OTHER INFORMATION: Synthetic (forward primer for L273W)

<400> SEQUENCE: 88
tcttttgata ataattggcc ttgtattgca                                    30

<210> SEQ ID NO 89
<211> LENGTH: 30
<212> TYPE: DNA
<213> ORGANISM: Artificial Sequence

```
<220> FEATURE:
<223> OTHER INFORMATION: Synthetic (reverse primer for L273W)

<400> SEQUENCE: 89
tgcaatacaa ggccaattat tatcaaaaga                                    30

<210> SEQ ID NO 90
<211> LENGTH: 30
<212> TYPE: DNA
<213> ORGANISM: Artificial Sequence
<220> FEATURE:
<223> OTHER INFORMATION: Synthetic (forward primer for L273Y)

<400> SEQUENCE: 90
tcttttgata ataattatcc ttgtattgca                                    30

<210> SEQ ID NO 91
<211> LENGTH: 30
<212> TYPE: DNA
<213> ORGANISM: Artificial Sequence
<220> FEATURE:
<223> OTHER INFORMATION: Synthetic (reverse primer for L273Y)

<400> SEQUENCE: 91
tgcaatacaa ggataattat tatcaaaaga                                    30

<210> SEQ ID NO 92
<211> LENGTH: 1000
<212> TYPE: DNA
<213> ORGANISM: Clostridium saccharoperbutylacetonicum
<220> FEATURE:
<221> NAME/KEY: NAD-dependent aldehyde dehydrogenase
<222> LOCATION: (1)..(1000)

<400> SEQUENCE: 92
atgattaaag acacgctagt ttctataaca aaagatttaa attaaaaac aaatgttgaa      60 aatgccaatc taaagaacta caaggatgat tcttcatgtt tcggagtttt cgaaaatgtt    120
gaaaatgcta taagcaatgc cgtacacgca caaaagatat tatcccttca ttatacaaaa    180
gaacaaagag aaaaaatcat aactgagata agaaaggccg cattagaaaa taagagatt     240 ctagctacaa tgattcttga agaaacacat atgggaagat atgaagataa aatattaaag    300
catgaattag tagctaaata cactcctggg acagaagatt taactactac tgcttggtca    360
ggagataacg ggcttacagt tgtagaaatg tctccatatg gcgttatagg tgcaataact    420
ccttctacga atccaactga aactgtaata tgtaatagta taggcatgat agctgctgga    480
aatactgtgg tatttaacgg acatccaggc gctaaaaat gtgttgcttt tgctgtcgaa    540
atgataaata agctattat ttcatgtggt ggtcctgaga atttagtaac aactataaaa    600
aatccaacta tggactctct agatgcaatt attaagcacc cttcaataaa actactttgc    660
ggaactggag ggccaggaat ggtaaaaacc ctcttaaatt ctggtaagaa agctataggt    720
gctggtgctg gaaatccacc agttattgta gatgatactg ctgatataga aaaggctggt    780
aagagtatca ttgaaggctg ttctttgat aataattac cttgtattgc agaaaaagaa     840
gtatttgttt ttgagaacgt tgcagatgat ttaatatcta acatgctaaa aaataatgct    900
gtaattataa atgaagatca agtatcaaag ttaatagatt tagtattaca aaaaaataat    960
gaaactcaag aatactctat aaataagaaa tgggtcggaa                         1000

<210> SEQ ID NO 93
<211> LENGTH: 30
```

```
<212> TYPE: DNA
<213> ORGANISM: Artificial Sequence
<220> FEATURE:
<223> OTHER INFORMATION: Synthetic (constitutive lac promoter of
      cat1-sucD-4hbd-cat2 module)

<400> SEQUENCE: 93 tttacactttt atgcttccgg ctcgtatgtt                                    30

<210> SEQ ID NO 94
<211> LENGTH: 1617
<212> TYPE: DNA
<213> ORGANISM: Artificial Sequence
<220> FEATURE:
<223> OTHER INFORMATION: Synthetic (cat1 gene)

<400> SEQUENCE: 94
atgagtaaag ggattaagaa ctcgcaacta aaaaaaaaaa atgtgaaggc cagtaatgtg      60
gcagaaaaga ttgaagagaa agttgaaaaa acggataagg ttgttgaaaa agccgctgag     120
gttacagaga acggattag aaacctgaag ctgcaggaga aagttgttac agcggatgtg      180
gcggctgata tgattgaaaa tggcatgatt gtggcaatca gcggttttac tccgtccggt     240
tatccaaagg aagtccctaa agcactgact aaaaaagtta atgccctgga ggaggagttc     300 aaggtcaccct tatataccgg gtcaagcacg ggggccgaca tcgacgggga atgggcaaag     360
gcaggaatca tagaacggcg tatcccctac cagacaaatt ctgacatgcg aaaaaaaata     420
aatgacggtt ctattaagta cgctgatatg catttaagcc atatggctca atatattaat     480
tattctgtca ttcctaaagt cgatatagct ataatagaag cggtagctat tacgaagaaa     540
gggatataaa ttccttcgac gggaattggc aataccgcga cttttgtgga aaacgcggac     600
aaagtgatag tggaaattaa cgaagcccaa ccgctggaat tggagggcat ggcagacata     660
tacacattaa aaaaccccccc gcgtagagag ccgattccaa tagttaatgc tggcaatcgc     720
atagggacca catatgtgac ctgtggctcg gaaaaaatct cgccatcgt catgacaaat      780 acgcaagaca aaacaagacc tcttacagag gtgtctcctg tatctcaggc catctccgac     840
aatctgatag ttttttttaa caaagaagtg gaagagggca aattacctaa aaacctgctc     900
cccatacagt caggagttgg tagtgtcgca aatgcggttt tggccggtct ttgtgaatca     960
aactttaaaa acctaagttg ttacacggag gttatccagg atagcatgct gaagcttata    1020
aaatgtggaa aagcagatgt ggtgtcaggc acctccataa gtccatcacc ggagatgctg    1080
cctgagttca tcaaggacat aaacttcttt agagaaaaga tagtattaag accacaggaa    1140
atcagcaata acccagagat agcacgcaga atcggtgtga tatccataaa caccgccttg    1200
gaagtagaca tatatggtaa tgtaaacagt acgcacgtta tgggaagcaa aatgatgaat    1260
ggcataggcg gttctggcga cttttgcccgc aatgcatatc tcactatctt cactacagag    1320
tctatcgcca aaaaaggcga tatctcaagc atagtgccta tggtatccca tgtggatcat    1380
accgaacatg atgtaatggt catcgttacc gaacagggag tagcggatct gcgcggtctt    1440
tctcctaggg aaaaggcggt ggctataatc gaaaattgcg ttcatccgga ctataaggat    1500
atgctgatgg agtattttga agaagcgtgc aaatcgtcag gtgggaacac cccacacaat    1560
cttgaaaaag ctctttcatg gcacacaaaa tttataaaaa cgggtagcat gaaataa      1617

<210> SEQ ID NO 95
<211> LENGTH: 1356
<212> TYPE: DNA
<213> ORGANISM: Artificial Sequence
```

```
<220> FEATURE:
<223> OTHER INFORMATION: Synthetic (sucD gene)

<400> SEQUENCE: 95
atggaaataa aagagatggt gtcgttggca aggaaagctc agaaggaata tcaagcgacc      60
cataatcaag aagcagttga taacatttgc cgagctgcag caaaagtgat ttatgaaaat     120
gcagctatac tggctcgcga agcagtagac gaaaccggca tgggcgtata tgaacataaa     180
gtggccaaga atcaggggaa atccaaaggc gtctggtaca atttgcacaa taaaaaatcg     240
atcggtatct aaatataga cgagagaacc gggatgatcg agatagcaaa acctatcggg     300
gttgttggag ccgtaacccc gacgacaaac ccgattgtga ctccaatgag caacatcatt     360 tttgcccttta agacatgcaa tgccattatt atcgccccac atcccagatc caaaaaatgc     420
tcagcacatg cagttcgtct gataaaggaa gcaatcgctc cgtttaatgt cccggaggga     480
atggttcaga tcattgaaga gcccagcatc gagaaaactc aggaactaat gggcgccgtg     540
gatgtggtag ttgcgacggg tggtatgggt atggtgaaat ctgcatattc ttcagggaag     600
ccttcttttg gtgtaggagc cggtaacgtt caagtgatcg tggatagtaa tatcgatttt     660
gaagctgcgg cagaaaaaat tatcaccggc cgtgctttcg acaatgggat catctgttca     720
ggcgaacaga gtatcatcta caacgaagct gacaaggaag ctgtcttcac agccttccgc     780
aaccatggtg catatttttg tgatgaagcg agggagatc gggcccgtgc tgcgatttt      840 gagaatggcg ccatcgcgaa agatgtagtc ggccagagcg ttgcctttat cgcgaagaaa     900
gcaaatatca atataccgga gggtacccgt attctggttg ttgaagctcg cggcgtcgga     960
gcagaggatg tcatatgtaa ggaaaaaatg tgtccagtta tgtgcgcctt aagctacaag    1020
cacttcgagg aaggtgtaga atcgcacgt acgaacttgg ccaacgaagg taacggccat    1080
acctgtgcga tccattccaa caatcaggcg catatcatac tggcaggttc agaactgacg    1140
gtttcgcgga tcgtggtcaa tgcgccgagt gccactacag caggcggtca catccaaaat    1200
ggtctggcag tgacaaatac gctcggatgc gggagttggg gtaataactc tatctccgag    1260
aactttactt ataaacacct gttaaacatt agccgcatag cgccgcttaa ttcaagcatt    1320
cacattcctg atgacaaaga gatctgggaa ctctaa                              1356

<210> SEQ ID NO 96
<211> LENGTH: 1116
<212> TYPE: DNA
<213> ORGANISM: Artificial Sequence
<220> FEATURE:
<223> OTHER INFORMATION: Synthetic (4hbd gene)

<400> SEQUENCE: 96
atgcaactgt tcaaactgaa atcagtcaca catcacttcg atactttcgc ggaatttgcc      60
aaagagttct gtcttggaga acgtgattta gtaattacca cgaattcat ttacgaaccg     120 tatatgaagg catgtcagtt gccctgccat tttgttatgc aggagaaata tgggcaaggc     180
gagccatctg acgagatgat gaataacatc ttggcagaca tccgtaatat ccagtttgac     240
cgcgtgatcg gtattggggg tggtacggtt attgacatct cgaaattatt tgtgctgaaa     300
ggactaaatg atgtgctcga tgcgttcgat cgcaagatac cgctgattaa agagaaagaa     360
ctgatcattg tgcccaccac atgcgggacg ggtagcgagg tgacgaatat ttcgatcgcg     420
gagatcaaaa gccgtcatac caaaatgggt ttggctgacg atgctattgt tgcagaccac     480
gcgatcatca taccagagct tctgaaaagc ctgccgttcc attttatgc atgcagtgca     540
```

```
atagatgctc tgatccatgc catcgagtca tatgtttctc ctaaagccag tccatattct      600
cgtctgttca gtgaggcggc atgggatatt atcctggagg tattcaagaa aatagccgaa      660
cacggccctg aataccgctt tgagaagctg ggagaaatga tcatggcctc caactatgct      720
ggtatagcct tcgggaatgc aggcgtgggt gccgttcacg ctctaagcta tccattggga      780
ggcaattatc atgtgccgca tggcgaggct aactatcagt tttttacaga ggtctttaaa      840
gtataccaaa agaaaaatcc tttcggctat atagtcgaac tcaactggaa gctgtccaag      900
attctgaact gtcagcctga atacgtctat ccgaaactgg atgagttact cggctgtctt      960
ctgaccaaaa aaccgctgca cgaataccgg atgaaagatg aagaggtacg tggatttgcg     1020
gaatcagtgc ttaagactca gcagcggttg ctcgcgaata attatgttga gcttactgtt     1080
gatgaaattg aaggtatcta cagacgactg tactaa                               1116
```

<210> SEQ ID NO 97
<211> LENGTH: 1296
<212> TYPE: DNA
<213> ORGANISM: Artificial Sequence
<220> FEATURE:
<223> OTHER INFORMATION: Synthetic (cat2 gene)

<400> SEQUENCE: 97

```
atgaaagacg tgttagcgga atatgcctcc cgaattgttt cggccgaaga ggcagtcaaa       60
catatcaaaa atggagagcg tgtcgcttta tcacatgctg ccggagttcc tcagagttgt      120
gttgacgcac tggtgcaaca ggcggacctg tttcagaatg tggagattta ccacatgctg      180
tgtctcggcg aaggaaaata tatggcacct gaaatggccc ctcacttccg gcacataacc      240
aattttgttg gtggtaactc tcgtaaagca gtggaggaaa atagagccga cttcattccg      300
gtattctttt atgaagtgcc atcaatgatt cggaaagata tccttcatat agatgtggcc      360
attgtccaac tctcaatgcc agatgagaat ggttactgca gctttggcgt atcttgcgat      420
tatagcaaac cggcggcgga atcggcgcat ttagttattg gggaaatcaa ccgtcagatg      480
ccatatgtgc atggtgacaa cttgattcac atatcgaagt tggattacat cgtgatggcg      540
gattacccaa tttattctct ggcgaagccc aaaatcggag aagtagagga agctatcggc      600
cgtaactgtg ccgagcttat tgaagatggt gccaccctac agctgggtat cggcgcgatt     660
ccggatgcag ctctgctgtt tctgaaggac aaaaaagatc tggggattca tactgaaatg      720
ttctccgatg gcgttgttga actggtgcgc agtggtgtaa ttactggaaa aaaaaagaca      780
ttgcatcccg gtaagatggt cgcgacgttt cttatgggat cagaagacgt gtatcatttc      840
atcgacaaga atccggatgt ggaactgtat ccggttgatt acgtcaatga tccgagggtt      900
atcgctcaga atgataatat ggtcagcatc aatagctgta tcgagatcga tctaatgggc      960
caagtggtga gcgagtgcat aggctccaaa cagtttagtg caccgggggg tcaagtagat     1020
tatgtccgcg gggcagcttg gtctaaaaac ggcaaaagca tcatggcaat tccctcaaca     1080
gccaaaaacg gtactgcatc tcggatagtt cctataattg cagagggcgc tgctgtaaca     1140 acccctccgca acgaagtcga ctacgttgtt acggaatatg ggatagcaca gttaaaaggt     1200
aagagtttgc gtcagcgcgc agaagctctt attgcgatag cccacccgga ctttagagag     1260
gaactgacga agcatctgcg caaacgtttt ggttaa                               1296
```

<210> SEQ ID NO 98
<211> LENGTH: 8613
<212> TYPE: DNA
<213> ORGANISM: Artificial Sequence
<220> FEATURE:
<223> OTHER INFORMATION: Synthetic (pSTV-cs4c full sequence)

<400> SEQUENCE: 98

| | | | | | | |
|---|---|---|---|---|---|---|
| cgtatggcaa | tgaaagacgg | tgagctggtg | atatgggata | gtgttcaccc | ttgttacacc | 60 |
| gttttccatg | agcaaactga | aacgttttca | tcgctctgga | gtgaatacca | cgacgatttc | 120 |
| cggcagtttc | tacacatata | ttcgcaagat | gtggcgtgtt | acggtgaaaa | cctggcctat | 180 |
| ttccctaaag | ggtttattga | gaatatgttt | ttcgtctcag | ccaatccctg | ggtgagtttc | 240 |
| accagttttg | atttaaacgt | ggccaatatg | gacaacttct | tcgcccccgt | tttcaccatg | 300 |
| ggcaaatatt | atacgcaagg | cgacaaggtg | ctgatgccgc | tggcgattca | ggttcatcat | 360 |
| gccgtttgtg | atggcttcca | tgtcggcaga | atgcttaatg | aattacaaca | gtactgcgat | 420 |
| gagtggcagg | gcggggcgta | attttttttaa | ggcagttatt | ggtgcccttt | aacgcctggt | 480 |
| gctacgcctg | aataagtgat | aataagcgga | tgaatggcag | aaattcgaaa | gcaaattcga | 540 |
| cccggtcgtc | ggttcagggc | agggtcgtta | aatagccgct | tatgtctatt | gctggtttac | 600 |
| cggtttattg | actaccggaa | gcagtgtgac | cgtgtgcttc | tcaaatgcct | gaggccagtt | 660 |
| tgctcaggct | ctccccgtgg | aggtaataat | tgacgatatg | atcatttatt | ctgcctccca | 720 |
| gagcctgata | aaaacggtta | gcgcttcgtt | aatacagatg | taggtgttcc | acagggtagc | 780 |
| cagcagcatc | ctgcgatgca | gatccggaac | ataatggtgc | agggcgcttg | tttcggcgtg | 840 |
| ggtatggtgg | caggccccgt | ggccggggga | ctgttgggcg | ctgccggcac | ctgtcctacg | 900 |
| agttgcatga | taaagaagac | agtcataagt | gcggcgacga | tagtcatgcc | ccgcgcccac | 960 |
| cggaaggagc | taccggacag | cggtgcggac | tgttgtaact | cagaataaga | aatgaggccg | 1020 |
| ctcatgcgt | tccaatacgc | aaaccgcctc | tccccgcgcg | ttggccgatt | cattaatgca | 1080 |
| gctggcacga | caggtttccc | gactggaaag | cgggcagtga | gcgcaacgca | attaatgtga | 1140 |
| gttagctcac | tcattaggca | ccccaggctt | tacactttat | gcttccggct | cgtatgttgt | 1200 |
| gtggaattgt | gagcggataa | caatttcaca | caggaaacag | ctatgaccat | gattacgaat | 1260 |
| tcgagctccc | gactgaaaag | cgggcagtga | gcgcaacgca | attaatgtga | gttagctcac | 1320 |
| tcattaggca | ccccaggctt | tacactttat | gcttccggct | cgtatgttgt | gtggaattgt | 1380 |
| gagcgtctag | aaggaggatt | acaaaatgag | taaagggatt | aagaactcgc | aactaaaaaa | 1440 |
| aaaaaatgtg | aaggccagta | atgtggcaga | aaagattgaa | gagaaagttg | aaaaaacgga | 1500 |
| taaggttgtt | gaaaaagccg | ctgaggttac | agagaaacgg | attagaaacc | tgaagctgca | 1560 |
| ggagaaagtt | gttacagcgg | atgtggcggc | tgatatgatt | gaaaatggca | tgattgtggc | 1620 |
| aatcagcggt | tttactccgt | ccggttatcc | aaaggaagtc | cctaaagcac | tgactaaaaa | 1680 |
| agttaatgcc | ctggaggagg | agttcaaggt | caccttatat | accgggtcaa | gcacgggggc | 1740 |
| cgacatcgac | ggggaatggg | caaaggcagg | aatcatagaa | cggcgtatcc | cctaccagac | 1800 |
| aaattctgac | atgcgaaaaa | aaataaatga | cggttctatt | aagtacgctg | atatgcattt | 1860 |
| aagccatatg | gctcaatata | ttaattattc | tgtcattcct | aaagtcgata | tagctataat | 1920 |
| agaagcggta | gctattacgg | aagaagggga | tataattcct | tcgacgggaa | ttggcaatac | 1980 |
| cgcgactttt | gtggaaaacg | cggacaaagt | gatagtggaa | attaacgaag | cccaaccgct | 2040 |
| ggaattggag | ggcatggcag | acatatacac | attaaaaaac | cccccgcgta | gagagccgat | 2100 |
| tccaatagtt | aatgctggca | atcgcatagg | gaccacatat | gtgacctgtg | gctcggaaaa | 2160 |
| aatctgcgcc | atcgtcatga | caaatacgca | agacaaaaca | agacctctta | cagaggtgtc | 2220 |

```
tcctgtatct caggccatct ccgacaatct gataggtttt ttaaacaaag aagtggaaga      2280
gggcaaatta cctaaaaacc tgctccccat acagtcagga gttggtagtg tcgcaaatgc      2340
ggttttggcc ggtctttgtg aatcaaactt taaaaaccta agttgttaca cggaggttat      2400
ccaggatagc atgctgaagc ttataaaatg tggaaaagca gatgtggtgt caggcacctc      2460
cataagtcca tcaccggaga tgctgcctga gttcatcaag gacataaact tctttagaga      2520
aaagatagta ttaagaccac aggaaatcag caataaccca gagatagcac gcagaatcgg      2580
tgtgatatcc ataaacaccg ccttggaagt agacatatat ggtaatgtaa acagtacgca      2640
cgttatggga agcaaaatga tgaatggcat aggcggttct ggcgactttg cccgcaatgc      2700
atatctcact atcttcacta cagagtctat cgccaaaaaa ggcgatatct caagcatagt      2760
gcctatggta tcccatgtgg atcataccga acatgatgta atggtcatcg ttaccgaaca      2820
gggagtagcg gatctgcgcg gtctttctcc tagggaaaag gcggtggcta taatcgaaaa      2880
ttgcgttcat ccggactata aggatatgct gatggagtat tttgaagaag cgtgcaaatc      2940
gtcaggtggg aacaccccac acaatcttga aaaagctctt tcatggcaca caaaattat       3000 aaaaacgggt agcatgaaat aatagaagga gatataaata tggaaataaa agagatggtg      3060
tcgttggcaa ggaaagctca gaaggaatat caagcgaccc ataatcaaga agcagttgat      3120
aacatttgcc gagctgcagc aaaagtgatt tatgaaaatg cagctatact ggctcgcgaa      3180
gcagtagacg aaaccggcat gggcgtatat gaacataaag tggccaagaa tcagggaaa       3240 tccaaaggcg tctggtacaa tttgcacaat aaaaaatcga tcggtatctt aaatatagac      3300
gagagaaccg ggatgatcga gatagcaaaa cctatcgggg ttgttggagc cgtaaccccg      3360
acgacaaacc cgattgtgac tccaatgagc aacatcattt ttgcccttaa gacatgcaat      3420
gccattatta tcgccccaca tcccagatcc aaaaaatgct cagcacatgc agttcgtctg      3480
ataaaggaag caatcgctcc gtttaatgtc ccggagggaa tggttcagat cattgaagag      3540
cccagcatca gaaaactcag gaactaatg ggcgccgtgg atgtggtagt tgcgacgggt       3600
ggtatgggta tggtgaaatc tgcatattct tcagggaagc cttcttttgg tgtaggagcc      3660
ggtaacgttc aagtgatcgt ggatagtaat atcgattttg aagctgcggc agaaaaaatt      3720
atcaccggcc gtgctttcga caatgggatc atctgttcag gcgaacagag tatcatctac      3780
aacgaagctg acaaggaagc tgtcttcaca gccttccgca accatggtgc atattttgt       3840 gatgaagcgg agggagatcg ggcccgtgct gcgattttg agaatggcgc catcgcgaaa       3900
gatgtagtcg gccagagcgt tgcctttatc gcgaagaaag caaatatcaa tataccggag      3960
ggtacccgta ttctggttgt tgaagctcgc ggcgtcggag cagaggatgt catatgtaag      4020
gaaaaaatgt gtccagttat gtgcgcctta agctacaagc acttcgagga aggtgtagaa      4080
atcgcacgta cgaacttggc caacgaaggt aacggccata cctgtgcgat ccattccaac      4140
aatcaggcgc atatcatact ggcaggttca gaactgacgg tttcgcggat cgtggtcaat      4200
gcgccgagtg ccactacagc aggcggtcac atccaaaatg gtctggcagt gacaaatacg      4260
ctcggatgcg ggagttgggg taataactct atctccgaga actttactta taaacacctg      4320
ttaaacatta gccgcatagc gccgcttaat tcaagcattc acattcctga tgacaaagag      4380
atctgggaac tctaatagaa ggagatataa atatgcaact gttcaaactg aaatcagtca      4440
cacatcactt cgatactttc gcggaatttg ccaaagagtt ctgtcttgga gaacgtgatt      4500
tagtaattac caacgaattc atttacgaac cgtatatgaa ggcatgtcag ttgccctgcc      4560
attttgttat gcaggagaaa tatgggcaag gcgagccatc tgacgagatg atgaataaca      4620
```

```
tcttggcaga catccgtaat atccagtttg accgcgtgat cggtattggg ggtggtacgg    4680
ttattgacat ctcgaaatta tttgtgctga aaggactaaa tgatgtgctc gatgcgttcg    4740
atcgcaagat accgctgatt aaagagaaag aactgatcat tgtgcccacc acatgcggga    4800
cgggtagcga ggtgacgaat atttcgatcg cggagatcaa aagccgtcat accaaaatgg    4860
gtttggctga cgatgctatt gttgcagacc acgcgatcat cataccagag cttctgaaaa    4920
gcctgccgtt ccattttat gcatgcagtg caatagatgc tctgatccat gccatcgagt     4980
catatgtttc tcctaaagcc agtccatatt ctcgtctgtt cagtgaggcg catgggata    5040 ttatcctgga ggtattcaag aaaatagccg aacacggccc tgaataccgc tttgagaagc    5100
tgggagaaat gatcatggcc tccaactatg ctggtatagc cttcgggaat gcaggcgtgg    5160
gtgccgttca cgctctaagc tatccattgg gaggcaatta tcatgtgccg catggcgagg    5220
ctaactatca gttttttaca gaggtcttta agtatacca aaagaaaaat cctttcggct     5280
atatagtcga actcaactgg aagctgtcca agattctgaa ctgtcagcct gaatacgtct    5340
atccgaaact ggatgagtta ctcggctgtc ttctgaccaa aaaaccgctg cacgaatacg    5400
gcatgaaaga tgaagaggta cgtggatttg cggaatcagt gcttaagact cagcagcggt    5460
tgctcgcgaa taattatgtt gagcttactg ttgatgaaat tgaaggtatc tacagacgac    5520
tgtactaata aaggagata taaatatgaa agacgtgtta gcggaatatg cctcccgaat     5580
tgtttcggcc gaagaggcag tcaaacatat caaaaatgga gagcgtgtcg ctttatcaca    5640
tgctgccgga gttcctcaga gttgtgttga cgcactggtg caacaggcgg acctgtttca    5700
gaatgtggag atttaccaca tgctgtgtct cggcgaagga aaatatatgg cacctgaaat    5760 ggccccctcac ttccggcaca taaccaattt tgttggtggt aactctcgta agcagtgga    5820 ggaaaataga gccgacttca ttccggtatt cttttatgaa gtgccatcaa tgattcggaa    5880
agatatcctt catatagatg tggccattgt ccaactctca atgccagatg agaatggtta    5940
ctgcagcttt ggcgtatctt gcgattatag caaaccggcg gcggaatcgg cgcatttagt    6000
tattggggaa atcaaccgtc agatgccata tgtgcatggt gacaacttga ttcacatatc    6060
gaagttggat tacatcgtga tggcggatta cccaatttat tctctggcga agcccaaaat    6120
cggagaagta gaggaagcta tcggccgtaa ctgtgccgag cttattgaag atggtgccac    6180
cctacagctg ggtatcggcg cgattccgga tgcagctctg ctgtttctga aggacaaaaa    6240
agatctgggg attcatactg aaatgttctc cgatggcgtt gttgaactgg tgcgcagtgg    6300
tgtaattact ggaaaaaaaa agacattgca tcccggtaag atggtcgcga cgtttcttat    6360
gggatcagaa gacgtgtatc atttcatcga caagaatccg gatgtggaac tgtatccggt    6420
tgattacgtc aatgatccga gggttatcgc tcagaatgat aatatggtca gcatcaatag    6480
ctgtatcgag atcgatctaa tgggccaagt ggtgagcgag tgcataggct ccaaacagtt    6540
tagtggcacc gggggtcaag tagattatgt ccgcggggca gcttggtcta aaaacgcaa     6600 aagcatcatg gcaattccct caacagccaa aaacggtact gcatctcgga tagttcctat    6660
aattgcagag ggcgctgctg taacaaccct ccgcaacgaa gtcgactacg ttgttacgga    6720
atatgggata gcacagttaa aaggtaagag tttgcgtcag cgcgcagaag ctcttattgc    6780
gatagcccac ccggacttta gagaggaact gacgaagcat ctgcgcaaac gttttggtta    6840
agcggccgct gcggtatttt ctccttacgc atctgtgcgg tatttcacac cggatcctct    6900
agagtcgacc tgcaggcatg caagcttggc actggccgtc gttttacaac gtcgtgactg    6960
```

```
ggaaaaccct ggcgttaccc aacttaatcg ccttgcagca catcccct   tcgccagctg    7020 gcgtaatagc gaagaggccc gcaccgatcg cccttcccaa cagttgcgca gcctgaatgg    7080
cgaatgagct tatcgatgat aagctgtcaa acatgagaat tacaacttat atcgtatggg    7140
gctgacttca ggtgctacat ttgaagagat aaattgcact gaaatctaga aatattttat    7200
ctgattaata agatgatctt cttgagatcg ttttggtctg cgcgtaatct cttgctctga    7260
aaacgaaaaa accgccttgc agggcggttt ttcgaaggtt ctctgagcta ccaactcttt    7320
gaaccgaggt aactggcttg gaggagcgca gtcaccaaaa cttgtccttt cagtttagcc    7380
ttaaccggcg catgacttca agactaactc ctctaaatca attaccagtg gctgctgcca    7440
gtggtgcttt tgcatgtctt tccgggttgg actcaagacg atagttaccg gataaggcgc    7500
agcggtcgga ctgaacgggg ggttcgtgca tacagtccag cttggagcga actgcctacc    7560
cggaactgag tgtcaggcgt ggaatgagac aaacgcggcc ataacagcgg aatgacaccg    7620
gtaaaccgaa aggcaggaac aggagagcgc acgagggagc cgccagggga aacgcctggt    7680
atctttatag tcctgtcggg tttcgccacc actgatttga gcgtcagatt tcgtgatgct    7740
tgtcaggggg gcggagccta tggaaaaacg gctttgccgc ggccctctca cttccctgtt    7800
aagtatcttc ctggcatctt ccaggaaatc tccgccccgt tcgtaagcca tttccgctcg    7860
ccgcagtcga acgaccgagc gtagcgagtc agtgagcgag gaagcggaat atatcctgta    7920
tcacatattc tgctgacgca ccggtgcagc cttttttctc ctgccacatg aagcacttca    7980
ctgacaccct catcagtgcc aacatagtaa gccagtatac actccgctag cgctgatgtc    8040
cggcggtgct tttgccgtta cgcaccaccc cgtcagtagc tgaacaggag ggacagctga    8100
tagaaacaga agccactgga gcacctcaaa aacaccatca tacactaaat cagtaagttg    8160
gcagcatcac ccgacgcact ttgcgccgaa taaatacctg tgacgaaga tcacttcgca     8220 gaataaataa atcctggtgt ccctgttgat accgggaagc cctgggccaa cttttggcga    8280
aaatgagacg ttgatcggca cgtaagaggt tccaactttc accataatga aataagatca    8340
ctaccgggcg tatttttga  gttatcgaga ttttcaggag ctaaggaagc taaaatggag    8400
aaaaaaatca ctggatatac caccgttgat atatcccaat ggcatcgtaa agaacatttt    8460
gaggcatttc agtcagttgc tcaatgtacc tataaccaga ccgttcagct ggatattacg    8520
gcctttttaa agaccgtaaa gaaaaataag cacaagtttt atccggcctt tattcacatt    8580
cttgcccgcc tgatgaatgc tcatccggaa ttt                                 8613
```